(12) United States Patent
Klem

(10) Patent No.: US 7,060,690 B2
(45) Date of Patent: Jun. 13, 2006

(54) METHODS AND COMPOSITIONS FOR TREATING A CELL-PROLIFERATIVE DISORDER USING CRE DECOY OLIGOMERS, BCL-2 ANTISENSE OLIGOMERS, AND HYBRID OLIGOMERS THEREOF

(75) Inventor: Robert E. Klem, Florham Park, NJ (US)

(73) Assignee: Genta Incorporated, Berkeley Heights, NJ (US)

( * ) Notice: Subject to any disclaimer, the term of this patent is extended or adjusted under 35 U.S.C. 154(b) by 511 days.

(21) Appl. No.: 10/053,645

(22) Filed: Jan. 22, 2002

(65) Prior Publication Data

US 2003/0176376 A1 Sep. 18, 2003

Related U.S. Application Data

(60) Provisional application No. 60/263,244, filed on Jan. 22, 2001.

(51) Int. Cl.
C07H 21/04 (2006.01)
A61K 48/00 (2006.01)
C12N 15/00 (2006.01)

(52) U.S. Cl. .................. 514/44; 536/24.1; 536/24.5; 435/6; 435/375; 435/377

(58) Field of Classification Search .............. 514/44; 536/24.1, 24.5; 435/6, 375, 377
See application file for complete search history.

(56) References Cited

U.S. PATENT DOCUMENTS

| | | | |
|---|---|---|---|
| 5,734,033 A | 3/1998 | Reed | |
| 5,831,066 A | 11/1998 | Reed | |
| 6,040,181 A | 3/2000 | Reed | |
| 6,060,310 A | 5/2000 | Cho-Chung | |

FOREIGN PATENT DOCUMENTS

| | | |
|---|---|---|
| WO | WO 88/09810 | 12/1988 |
| WO | WO 89/10134 | 11/1989 |

OTHER PUBLICATIONS

Ameis et al., 1990, "Isolation and Characterization of the Human Hepatic Lipase Gene," J Biol Chem. 265(12):6552-6555.
Asseline et al., 1984, "Nucleic acid-binding molecules with high affinity and base sequence specificity: Intercalating agents covalently liked to oligodeoxynucleotides," Proc. Natl Acad. Sci. USA 81:3297-3301.
Bishop, The Molecular Genetics of Cancer,"citing Cellular Oncogenes and Retroviruses," Science, 235:305-311 (1987).
Blake et al., 1985, "Inhibition of Rabbit Globin mRNA Translation by Sequence-Specific Oligodeoxyribonucleotides," Biochemistry 24:6132-38.
Boutorin et al., 1984, "Complementary addressed reragents carrying EDTA-Fe(II) groups for directed cleavage of single-stranded nucleic acids," FEBS Letters 172:43-6.
Brown et al., 1987, "*lac* Repressor Can Regulate Expression From A Hybrid SV40 Early Promoter Containing A Lac Operator In Animal Cells," Cell 49(5):603-612.
Burt et al., 1989, "Identification Of Negative And Positive Regulatory Elements In The Human Renin Gene," J Biol Chem. 264(13):7357-62.
Changelian et al., 1989, "Structure of the NGFI-A gene and detection of upstream sequences responsible for its transcriptional induction by nerve growth factor," Proc Natl Acad Sci USA 86(1):377-81.
Chen et al., 1986, "Nuclease activity of 1,10-phenanthroline-copper: Sequence-specific targeting," Proc. Natl. Acad. Sci. USA 83:7147-51.
Cho-Chung, 1998, "CRE-Palindrome Oligonucleotide As A Transcription Factor Decoy And An Inhibitor Of Tumor Growth," Antisense Nucleic Acid Drug Dev. 8(2):167-70.
Chu et al., 1985, "Nonenzymatic sequence-specific cleavage of single-stranded DNA," Proc. Natl. Acad. Sci. USA 82:963-7.
Comb et al., 1986, "A cyclic AMP- and phorbol ester-inducible DNA element," Nature 323:353.
Desbarats et al., 1992, "Identification of a Unique cAMP-Response Element in the Gene Encoding the Cell Adhesion Molecule Gp80 In *Dictyostelium Discoideum*," J Biol Chem. 267(27):19655-64.
Egholm et al., 1992, "Peptide Nucleic Acids (PNA)-Oligomer Analogues With An Achiral Peptide Backbone" J. Am. Chem. Soc. 114:1895-1897.

(Continued)

*Primary Examiner*—Sean McGarry
(74) *Attorney, Agent, or Firm*—Kenyon & Kenyon LLP

(57) ABSTRACT

The present invention is directed to hybrid oligomers comprising a cyclic AMP response element (CRE) sequence and a sequence that hybridizes to a bcl-2 pre-mRNA or mRNA, and pharmaceutical compositions comprising such hybrids. The present invention is also directed to the use of CRE decoy oligomers, comprising a CRE consensus sequence, and bcl-2 antisense oligomers in combination therapies, and the use of bcl-2/CRE hybrid oligomers, to treat or prevent cell-proliferative related disorders, including hyperplasias, cancers, tumors and carcinomas. In one embodiment, the invention relates to therapeutic protocols comprising the administration of a CRE decoy oligomer and a bcl-2 antisense oligomer for the treatment of cell-proliferative related disorders. In another embodiment, the invention relates to therapeutic protocols comprising the administration of a bcl-2 antisense/CRE decoy (bcl-2/CRE) hybrid oligomer for the treatment of cell-proliferative related disorders.

48 Claims, No Drawings

OTHER PUBLICATIONS

Freeland et al., 1988, "Nucleotide sequence of the region upstream of the rat growth hormone gene," GenBank Accession No. X12967.

Gautier et al., 1987, α-DNA IV: α-anomeric and β-anomeric tetrathymidylates covalently linked to intercalating oxazolopyridocarbazole. Synthesis, physicochemical properties and poly (rA) vbinding, Nucleic Acids Res. 15:6625-6641.

Goodchild, 1990, "Conjugates Of Oligonucleotides And Modified Oligonucleotides: A Review Of Their Synthesis And Properties," Bioconjug. Chem. 1(3):165-87.

Hla and Neilson, 1992 "Human cyclooxygenase-2 cDNA," Proc Natl Acad Sci USA 89(16):7384-8.

Hu and Davidson, 1988, "The inducible *lac* operator-repressor system is functional for control of expression of injected DNA in *Xenopus oocytes*," Gene. 62(2):301-13).

Hyrup et al., 1996, "Peptide Nucleic Acids (PNA): Synthesis, Properties and Potential Applications," Bioorganic & Medicinal Chemistry 4(1): 5-23.

Inoue et al., 1987, "Sequence-dependent hydrolysis of RNA using modified oligonucleotide splints and RNase H," FEBS Lett. 215:327-30.

Inoue et al., 1987, "Synthesis and hybridization studies on two complementary nona(2'-O-methyl)ribonucleotides," Nucleic Acids Res. 15:6131-48.

Izuhara et al., 1995, "Transcription of the rat liver uricase-encoding gene is regulated via a cis-acting element responsive to cAMP," Gene. 167(1-2):267-72.

Jansen et al., 1995, "Neuroendocrine-Specific Expression of the Human Prohormone Convertase I Gene: Hormonal Regulation of Transcription through Distinct cAMP Response Elements," J Biol Chem. 270(25):15391-7.

Knorre et al., 1985, "Reactive oligonucleotide derivatives and sequence-specific modification of nucleic acids," Biochemie 67:785-9.

Kobayashi K, Kurosawa Y, Fujita K, Nagatsu T., 1989, "Human dopamine β-hydroxylase gene: two mRNA types having different 3'-terminal regions are produced through alternative polyadenylation," Nuc Acids Res. 17(3):1089-1102.

Lemaitre et al., 1987, "Specific antiviral activity of a poly(L-lysine)-conjugated oligodeoxyribonucleotide sequence complementary to vesicular stomatitis virus N protein mRNA initiation site," Proc. Natl. Acad. Sci. USA 84:648-52.

Letsinger et al., 1989, "Cholesteryl-conjugated oligonucleotides: synthesis, properties, and activity as inhibitors of replication of human immunodeficiency virus in cell culture," Proc. Natl. Acad. Sci. USA 86:6553-6.

Mahata et al., 1996, "Dispersion of Chromogranin/Secretogranin Secretory Protein Family Loci in Mammalian Genomes," Genomics 33(1):135-9.

Miller et al., 1988, "Structure of a Gap Junction Gene: Rat Connexin-32," Biosci Rep. 8(5):455-64.

Monia et al., 1993, "Evaluation of 2'-Modified Oligonucleotides Containing 2' Deoxy Gaps as Antisense Inhibitors of Gene Expression," J. Biol. Chem. 268:14514-22.

Morishita et al., 1998, "Application of Transcription Factor 'decoy' Strategy as Means of Gene Therapy and Study of Gene Expression in Cardiovascular Disease," Circ Res. 82(10):1023-8.

Morvan et al., 1986, alpha-DNA. 1. Synthesis, characterization by high field 1H-NMR, and base-pairing properties of the unnatural hexadeoxyribonucleotide alpha-[d(CpCpTpTpCpC)] with its complement beta-[d(GpGpApApGpG)]. Nucl. Acids Res. 14:5019-32.

Nielsen et al., 1993, "Peptide nucleic acids (PNAs): Potential antisense and anti-gone agents," Anticancer Drug Des 8:53-63.

Ogawa et al., 1994, "Molecular Cloning and Chromosomal Assignment of the Mouse C-Type Natriuretic Peptide (CNP) Gene (Nppc): Comparison with the Human CNP Gene (NPPC)" Genomics 24(2):383-7.

Ogawa et al., 1995, "Characterization of the 5'-flanking region and chromosomal assignment of the human brain natriuretic peptide gene," J Mol Med. 73(9):457-63.

Park et al., 1999, "Dual Blockade of Cyclic AMP Response Element-(CRE) and AP-1-Directed Transcription by CRE-Transcription Factor Decoy Oligonucleotide Gene-Specific Inhibition of Tumor Growth," J. Biol. Chem. 274:1573-80.

Perez-Albuerne et al., 1993, "Transcriptional regulatory elements downstream of the JunB gene," Proc. Natl. Acad. Sci. USA 90(24):11960-4.

Sarabia and Liehr, 1999, "Differential Regulation of C-Fos Expression in Estrogen-Induced Hamster Renal Tumors Compared With Kidney Not Due To Creation of an Estrogen-Response Element by Point Mutation in the Gene's Flanking Sequence," Mol Carcinog. 24(4):255-62.

Schmoll et al., 1999, "Identification of a cAMP response element within the glucose-6-phosphatase hydrolytic subunit gene promoter which is involved in the transcriptional regulation by cAMP and glucocorticoids in H4IIE hepatoma cells," Biochem J. 338 (Pt.2):457-63.

Sensel et al., 1990, "Isolation and characterization of clones for the rat hepatic lipase gene upstream regulatory region" Biochim Biophys Acta. 1048:297-302.

Short et al., 1986, "Characterization of the Phosphoenolpyruvate Carboxykinase (GTP) Promoter-regulatory Region. II. Identification of cAMP and Glucocorticoid Regulatory Domains," J. Biol. Chem. 261:9721-6.

Stein et al., 1988, "Physicochemical properties of phosphorothioate oligodeoxynucleotides," Nucl. Acids Res., 16:3209-21.

Thomas et al., 1990, "Z-DNA formation in the rat growth hormone gene promoter region," Mol Cell Biol. 10(10):5378-87.

Tomita et al., 1997, "A Novel Strategy for Gene Therapy and Gene Regulation Analysis Using Transcription Factor Decoy Oligonucleotides," Exp Nephrol. 5(5):429-34.

Tsujimoto et al., "Involvement of the bcl-2 gene in Human Follicular Lymphoma," Science 228:1440-3 (1985).

Tsukada et al., 1987, "Identification of a Region in the Human Vasoactive Intestinal Polypeptide Gene Responsible for Regulation by Cyclic AMP," J. Biol. Chem. 262:8743.

Van der Krol et al., 1988, "Modulation of Eukaryotic Gene Expression by Complementary RNA or DNA Sequences," BioTechniques 6:958-976-7.

VanBeveren et al., 1983, "Analysis of FBJ-MuSV Provirus and c-fos (Mouse) Gene Reveals That Viral and Cellular fos Gene Products Have Different Carboxy Termini," Cell 32:1241-55.

Verma and Eckstein, 1998, "Modified Oligonucleotides: Synthesis and Strategy for Users," Annu Rev Biochem. 67:99-134.

Virkkunen et al., 1994, "Structural Comparison Of Human And Rat Prostate-Specific Acid Phosphatase Genes And Their Promoters: Identification of Putative Androgen Response Elements," Biochem Biophys Res Commun. 202(1):49-57.

Vitale et al., 1991, "Molecular cloning of the mouse CCK gene: expression in different brain regions and during cortical development," Nucleic Acids Res. 19(1):169-77.

Vlassov et al., 1986, "Complementary addressed modification and cleavage of a single stranded DNA fragment with alkylating oligonucleotide derivatives," Nucl. Acids Res. 14:4065-76.

Webb et al., 1986, "Hybridization triggered cross-linking of deoxyoligonucleotides," Nucl. Acids Res. 4:7661-74.

Yao et al., 1999, "Molecular Cloning and Sequence Analysis of the 5'-Flanking Region of the Sprague-Dawley Rat Thrombomodulin Gene," DNA Seq. 10(1):55-60.

Yokoyama et al., 1991, "Molecular Cloning of Human Platelet Thromboxane A Synthase," Biochem Biophys Res Comm. 178(3):1479-84.

Zhu et al., 1992, "Promoter Organization and Activity of Human Monoamine oxidase (MAO) A and B Genes," J Neurosci. 12(11):4437-46.

Zon, 1988, "Oligonucleotide Analogues as Potential Chemotherapeutic Agents," Pharm. Res. 5:539-549.

Alper et al., 2001, "Apoptosis, Growth Arrest And Suppression Of Invasiveness By CRE-Decoy Oligonucleotide In Ovarian Cancer Cells: Protein Kinase A Downregulation And Cytoplasmic Export Of CRE-Binding Proteins," Mol. Cell. Biochem. 218:55-63.

Cho, et al., 2000, "Biochemical Characterization Of Extracellular cAmp-Dependent Protein Kinase As A Tumor Marker," Biochem. and Biophys. Res. Comm. 278:679-684.

Cho-Chung et al., 2000, "CRE-Decoy Oligonucleotide-Inhibition of Gene Expression and Tumor Growth," Mol. and Cell. Biochem. 212:29-34.

Cho-Chung et al., 1999, "Oligonucleotides as Transcription Factor Decoys," Curr. Opin. Mol. Ther. 1(3):386-392.

Lee et al., 2000, "CRE-Transcription Factory Decoy Oligonucleotide Inhibition Of MCF-7 Breast Cancer Cells: Cross-Talk With p53 Signaling Pathway," Biochem. 39:4863-4868.

Park et al., 2001, "Reduction In Cyclin D1/Cdk4/ Retinoblastoma Protein Signaling By CRE-Decoy Oligonucleotide," Biochem. and Biophys. Comm. 281:1213-1219.

METHODS AND COMPOSITIONS FOR TREATING A CELL-PROLIFERATIVE DISORDER USING CRE DECOY OLIGOMERS, BCL-2 ANTISENSE OLIGOMERS, AND HYBRID OLIGOMERS THEREOF

This application claims the benefit of U.S. Provisional Patent Application Ser. No. 60/263,244, filed Jan. 22, 2001.

1. INTRODUCTION

The present invention relates to methods of preventing or treating a cell-proliferative related disorder which comprises targeting both the expression of a bcl-2 oncogene and the activity of transcription factors that can recognize cyclic AMP response elements (CRE). In particular, the present invention relates to a method of preventing or treating a cell-proliferative related disorder which method comprises administering a combination of a bcl-2 antisense oligomer and a CRE decoy oligomer to a subject in need of such treatment. The present invention also relates to pharmaceutical compositions comprising a bcl-2 antisense oligomer and a CRE decoy oligomer. In addition, the invention relates to hybrid oligomers with dual activities, which include the ability to hybridize to a bcl-2 mRNA, and the ability to compete with CRE enhancers for binding to transcription factors, thus modulating the transcriptional activity of sequence-specific DNA-binding proteins. The present invention also relates to methods of treatment and pharmaceutical compositions comprising said hybrid oligomers.

2. BACKGROUND OF THE INVENTION

2.1 Bcl-2 Antisense Oligomers

Traditional approaches to cancer treatment suffer from a lack of specificity. Most drugs that have been developed are natural products or derivatives which block enzyme pathways or randomly interact with DNA. Moreover, most cancer treatment drugs are accompanied by serious dose-limiting toxicities due to low therapeutic indices. For example, the majority of anti-cancer drugs, when administered to a patient, kill not only cancer cells but also normal, non-cancerous cells. Because of these deleterious effects, treatments that more specifically affect cancerous cells are needed.

Antisense oligodeoxynucleotides are one example of a specific therapeutic tool with the potential for ablating gene function relating to cell growth and division. These short (usually about 30 bases) single-stranded synthetic DNAs have a base sequence that is at least partly complementary to the target mRNA, and form a hybrid duplex by hydrogen-bonded base pairing with the target mRNA. This hybridization can be expected to hinder translation of the target mRNA into its protein product, and thereby reduce or preclude subsequent effects of the protein product. Because the mRNA sequence expressed by the gene is termed the sense sequence, the essentially complementary sequence is termed the antisense sequence. Since one mRNA molecule gives rise to multiple protein copies, inhibition of mRNA can be more efficient than inhibition of an enzyme's active site, under some circumstances.

Thus, antisense oligomers can be useful for disrupting oncogene expression. The oncogenes play a large role in the transformation and maintenance of the cancerous state such that turning off these genes, or otherwise inhibiting their effects, can return a cell to a normal phenotype. The role of oncogenes in the etiology of many human cancers has been reviewed in Bishop, "Cellular Oncogenes and Retroviruses," Science, 235:305–311 (1987). In many types of human tumors, including lymphomas and leukemias, the human bcl-2 gene is overexpressed, and may be associated with tumorigenicity (Tsujimoto et al., "Involvement of the bcl-2 gene in human follicular lymphoma", Science 228: 1440–1443 (1985)). The human bcl-2 gene is, therefore, a potentially useful therapeutic target.

2.2 CRE Decoy Oligomers

The displacement of a modulator protein from transcriptional regulatory sites provides a strategy for gene-specific activation or repression. For example, procaryotic repressors can function as negative regulators of eukaryotic promoters (Brown et al., 1987, "lac repressor can regulate expression from a hybrid SV40 early promoter containing a lac operator in animal cells", Cell 49(5):603–612; Hu and Davidson, 1988, "The inducible lac operator-repressor system is functional for control of expression of injected DNA in Xenopus oocytes", Gene. 62(2):301–313). Trans-dominant mutants, which retain the ability to bind to cis-regulatory DNA sequences (e.g. enhancers) but lack functional transcriptional activation domains, can also be designed to regulate gene expression through such displacement. These mutant transcription factors compete with their functional, wild-type counterparts for binding to the enhancer sequences, and thereby modulate the activation or repression of the target gene.

Another alternative is to introduce intracellularly, oligomers with high affinity for a nucleic acid binding protein (e.g., a transcription factor). Such oligomers can act as decoy cis-elements which can bind to, for example, a target transcription factor and thereby alter gene expression (Tomita et al., 1997, "A novel strategy for gene therapy and gene regulation analysis using transcription factor decoy oligonucleotides", Exp Nephrol. 5(5):429–34; Morishita et al., 1998, "Application of transcription factor "decoy" strategy as means of gene therapy and study of gene expression in cardiovascular disease", Circ Res. 82(10):1023–8). For instance, oligomers comprising nucleic acid molecules that compete with cyclic AMP response element (CRE) enhancers for binding to transcription factors can be designed to alter the expression of genes containing CRE enhancer regulatory sequences (Cho-Chung, 1998, "CRE-palindrome oligonucleotide as a transcription factor decoy and an inhibitor of tumor growth", Antisense Nucleic Acid Drug Dev. 8(2):167–70).

Thus, CRE decoy oligomers can be useful for inhibiting cancer cell growth, without adversely affecting the growth of noncancerous cells (Park et al., 1999, "Dual blockade of cyclic AMP response element-(CRE) and AP-1-directed transcription by CRE-transcription factor decoy oligonucleotide gene-specific inhibition of tumor growth", J. Biol. Chem. 274:1573–1580). The CRE-transcription factor complex is a pleiotropic activator that participates in the induction of a wide variety of cellular and viral genes. Therefore, modulation of CRE enhancer-driven transcription potentially has several therapeutic applications.

However, the art remains in need of means for regulating target gene expression to control and treat human diseases, such as cancer and viral infections.

3. SUMMARY OF THE INVENTION

The present invention relates to methods of preventing or treating a cell-proliferative related disorder, in particular cancer, comprising administering to a subject, in need of such prevention or treatment, a combination of oligomers that target a bcl-2 oncogene pre-mRNA and/or mRNA (e.g. bcl-2 antisense oligonucleotides) with oligomers which target transcription factors that recognize CREs (i.e., CRE decoys). In accordance with the methods of prevention and treatment of the present invention, the bcl-2 antisense oligomers and CRE decoy oligomers may be administered concurrently or sequentially. In a further embodiment, the bcl-2 antisense oligomers and CRE decoy oligomers may be administered in combination with other cancer therapeutics.

In accordance with the present invention, a bcl-2 antisense oligomer is an oligomer that can hybridize to a bcl-2 mRNA and/or bcl-2 pre-mRNA or a portion thereof. The target mRNA or pre-mRNA can include non-coding regulatory regions as well as coding regions of the unprocessed, primary bcl-2 transcript. The bcl-2 antisense oligomer can hinder or disrupt the production of the Bcl-2 polypeptide.

In accordance with the present invention, a CRE decoy oligomer is an oligomer that has the ability to bind to transcription factors capable of recognizing CREs, or CRE-like sequences. The CRE decoy can hinder or prevent binding of a transcription factor to an endogenous CRE enhancer. Thus, CRE decoys, in effect can modulate the transcriptional activity of sequence-specific DNA-binding proteins, and can be useful for regulating the expression of a wide variety of cellular and viral genes.

The present invention encompasses pharmaceutical compositions comprising combinations of bcl-2 antisense oligomers and CRE decoy oligomers for the treatment of a cell-proliferative disorder, including cancer, hyperplasia, or tumorigenesis. The present invention also encompasses pharmaceutical compositions comprising bcl-2 antisense oligomers and/or CRE decoy oligomers, in combination with other cancer therapeutics, for the treatment of abnormal cell growth, cancer, or tumorigenesis.

The present invention also relates to bcl-2/CRE hybrid oligomers with dual activities which include the ability to hybridize to a bcl-2 mRNA and/or pre-mRNA, and the ability to compete with CRE or CRE-like enhancers for binding to transcription factors. In a particular embodiment, the present invention encompasses hybrid oligomers comprising a bcl-2 antisense oligomer linked to a CRE decoy oligomer. The present invention also encompasses pharmaceutical compositions comprising said hybrid oligomers. The present invention also relates to methods of preventing or treating cell-proliferative related disorders, e.g., cancer and hyperplasia, comprising administering bcl-2/CRE hybrid oligomers, or pharmaceutical compositions thereof, to a subject in need of such treatment.

The present invention is also directed to methods of preventing or treating a cell-proliferative related disorder, in particular cancer, further comprising administering other cancer therapeutic agents in combination with the oligomers of the invention. In one embodiment, one or more bcl-2/CRE hybrid oligomers, CRE decoy oligomers, bcl-2 anti sense oligomers, and/or chemoagents are administered to a patient to prevent or treat a cell-proliferative related disorder. For example, a bcl-2/CRE hybrid oligomer and a chemoagent can be administered sequentially to treat a cancer.

The present invention is also drawn to the use of bcl-2 antisense and CRE decoy oligomers, and/or one or more bcl-2/CRE hybrid oligomers to increase the sensitivity of a subject to additional cancer therapeutics. In a particular embodiment, one or more bcl-2/CRE hybrid oligomers, bcl-2 antisense oligomers and/or CRE decoy oligomers are administered to a cancer patient to potentiate concurrent or subsequent treatment with chemoagents and/or oligomers of the present invention. Moreover, treatment with bcl-2/CRE hybrid oligomers, bcl-2 antisense oligomers, and/or CRE decoy oligomers can increase the sensitivity of cancerous tissue to the oligomers of the invention and/or chemotherapeutic agents such that lower doses and/or shorter treatment schedules have therapeutic effect, thereby reducing the toxicity of such treatments as compared with standard treatment protocols.

These and other aspects of the present invention will be better appreciated by reference to the following Figures and Detailed Description.

3.1. Definitions

As used herein, the term "cyclic AMP responsive element" or "CRE" refers to enhancer sequences which mediate signal transduction involving cAMP by interacting with transcription factors and/or associated proteins of the transcriptional complex. These sequences (some which bind to cAMP) include, but are not limited to, non-native sequences, consensus sequences (e.g., 5'-TGACGTCA-3'), as well as CREs, CRE-like sequences, and putative CREs that are associated with native genes. These sequences may comprise, for example, TTACGTCA (Short et al., 1986, "Characterization of the phosphoenolpyruvate carboxykinase (GTP) promoter-regulatory region. II. Identification of cAMP and glucocorticoid regulatory domains", J. Biol. Chem. 261:9721), TGACGTCT (Tsukada et al., 1987, "Identification of a region in the human vasoactive intestinal polypeptide gene responsible for regulation by cyclic AMP", J. Biol. Chem. 262:8743), TGACGTAG (VanBeveren et al., 1983, "Analysis of FBJ-MuSV provirus and c-fos (mouse) gene reveals that viral and cellular fos gene products have different carboxy termini", Cell 32:1241), CTGCGTCA (Comb et al., 1986, Nature 323:353), TGACGTCA (Mahata et al., 1996, "Dispersion of chromogranin/secretogranin secretory protein family loci in mammalian genomes", Genomics 33(1):135–9), TGCGTCAGC (X59520; Vitale et al., 1991, "Molecular cloning of the mouse CCK gene: expression in different brain regions and during cortical development", Nucleic Acids Res. 19(1): 169–77), TGACG, CGTCA (D34613; Yokoyama et al., 1991, "Molecular cloning of human platelet thromboxane A synthase", Biochem Biophys Res Comm. 178(3):1479–84), TGACATCA (D28873; Ogawa et al., 1994, "Molecular cloning and chromosomal assignment of the mouse C-type natriuretic peptide (CNP) gene (Nppc): comparison with the human CNP gene (NPPC)" Genomics 24(2):383–7), GTCGTCA, TCGTCAC (D28235; Hla and Neilson, 1992 "Human cyclooxygenase-2 cDNA", Proc Natl Acad Sci USA 89(16): 7384–8), TCCCAGGC (AF)22742; Yao et al., 1999, "Molecular cloning and sequence analysis of the 5-flanking 5 region of the Sprague-Dawley rat thrombomodulin gene", DNA Seq. 10(1): 55–60), (D16641, D28874; Ogawa et al., 1995, "Characterization of the 5'-flanking region and chromosomal assignment of the human brain natriuretic peptide gene", J Mol Med. 73(9):457–63; a nucleotide sequence comprising –161 to –152 of the glucose-6-phosphatase hydrolytic subunit gene promoter (AF051355; Schmoll et al., 1999, "Identification of a cAMP response element within the glucose-6-phosphatase hydrolytic subunit gene promoter which is involved in the transcriptional regulation by cAMP and glucocorticoids in H4IIE hepatoma cells", Biochem J. 338 (Pt 2):457–63), TGACGTG (AF061881; Sarabia and Liehr, 1999, "Differential regulation of c-fos expression in estrogen-induced hamster renal tumors compared with kidney not due to creation of an estrogen-response element by point mutation in the genes flanking sequence", Mol Carcinog. 24(4):255–62), CTGACGTCA (AF023677; Hardy S H, Walker S J, Goodman R L and Vrana K E), sequences comprising a portion (e.g., at least 5, 6, 7, 8, 9, 10, 11, 12, 13, 14, 15, 16, 17, 18, 19 or 20 consecutive nucleotides) of TTCAGCAAAAATGTCGACATATCTTCCA-CACCCCCCTGGTTCTGACCTCTCAGCAAG GCATTTGGCTTTGAAAGGCCGTTTTGT (SEQ ID NO:30; D50689; Izuhara et al., 1995, "Transcription of the rat liver uricase-encoding gene is regulated via a cis-acting element responsive to cAMP", Gene. 167(1–2):267–72), TGACCTCA (M89636; Zhu et al., 1992, "Promoter organization and activity of human monoamine oxidase (MAO) A and B genes", J Neurosci. 12(11):4437–46), a nucleotide sequence comprising −306 to −289 of the Dictyostelium gp80 gene (X66483, S45379; Desbarats et al., 1992, "Identification of a unique cAMP-response element in the gene encoding the cell adhesion molecule gp80 in Dictyostelium discoideum", J Biol Chem. 267(27): 19655–64), TGAGCTCA, sequences comprising a portion of (e.g., at least 5, 7, 10, 14, 16, 18 or 20 consecutive nucleotides) GACCGCATTTTCAAAAAGCTGCTCT-GAGAGTAGATGACGTAAATAAAGCCCTTGTAA CAGTGACGTA (SEQ ID NO:31; X17367; Sensel et al., 1990, "Isolation and characterization of clones for the rat hepatic lipase gene upstream regulatory region" Biochim Biophys Acta. 1048:297–302), CGTCA (X74961; Virkkunen et al., 1994, "Structural comparison of human and rat prostate-specific acid phosphatase genes and their promoters: identification of putative androgen response elements", Biochem Biophys Res Commun. 202(1):49–57), TGACGTCC (X13257; Kobayashi K, Kurosawa Y, Fujita K, Nagatsu T., 1989, "Human dopamine beta-hydroxylase gene: two mRNA types having different 3-terminal regions are produced through alternative polyadenylation.", Nuc Acids Res. 17(3):1089–1102), CTGACATCAC (SEQ ID NO:24, Freeland et al., 1988, "Nucleotide sequence of the region upstream of the rat growth hormone gene") (X12967; Thomas et al., 1990, "Z-DNA formation in the rat growth hormone gene promoter region", Mol Cell Biol. 10(10): 5378–87), AGACGTCA (X57155; Sanders L, McLane M W and Schatteman G C; Perez-Albuerne et al., 1993, "Transcriptional regulatory elements downstream of the JunB gene", Proc Natl Acad Sci USA 90(24):1 1960–4), TGA-CATCA, CTGACACCAG (SEQ ID NO:25) (M23565; Miller et al., 1988, "Structure of a gap junction gene: rat connexin-32", Biosci Rep. 8(5):455–64), TGACGTCA, TGACGTGT (U24128; Jansen et al., 1995, "Neuroendocrine-specific expression of the human prohormone convertase 1 gene: Hormonal regulation of transcription through distinct cAMP response elements", J Biol Chem. 270(25): 15391–7), TCACGTCAC (J04154; Changelian et al., 1989, "Structure of the NGFI-A gene and detection of upstream sequences responsible for its transcriptional induction by nerve growth factor", Proc Natl Acad Sci USA 86(1):377–8 1), a nucleotide sequence comprising a portion of CCCT-TCACCCACCTAGCTCTGTCCCGCAG (SEQ ID NO:32; M26440; Burt et at, 1989, "Identification of negative and positive regulatory elements in the human renin gene", J Biol Chem. 264(13):7357–62),. and TTCGTCA (M35425, J05432; Ameis et al., 1990, "Isolation and characterization of the human hepatic lipase gene", J Biol Chem. 265(12): 6552–6555). Moreover, these sequences encompass variants of known CRE sequences, resulting from e.g., base substitution(s), addition(s) or deletion(s), and derivatives or analogues thereof. Each of the above references is incorporated herein by reference in its entirety.

CRE-binding proteins may include transcription factors and associated proteins found in the transcriptional complex. These proteins include those which may not directly bind to a CRE but are bound to, or interact with, a protein that can directly bind to a CRE. Furthermore, these proteins need not be present at the CRE enhancer, but may be transiently associated with other proteins of the transcription complex before or after localization to a CRE.

As used herein, the term "bcl-2/CRE" refers to a hybrid molecule comprising a CRE sequence and a sequence that hybridizes to a bcl-2 pre-mRNA and/or bcl-2 mRNA. The bcl-2 pre-mRNA or bcl-2 mRNA is preferably human.

As used herein, the term "pre-mRNA" refers to a primary gene transcript from which the corresponding mRNA may be formed by post-transcriptional processing of the pre-mRNA.

As used herein, the term "derivative" refers to any pharmaceutically acceptable homolog, analogue, or fragment corresponding to the composition of the invention.

As used herein, the phrase "cell-proliferative disorder" refers to a condition marked by aberrant (e.g., uncontrolled) cell division. Such a disorder encompasses diseases involving cell division induced by, or concomitant with, for example, bacterial infections, viral infections, inflammation, inflammatory conditions (e.g., anaphylaxis, allergy, arthritis, asthma, microbial infection, parasitic infection), and autoimmune disorders. For example, a patient with an autoimmune disease may be treated using the methods and compositions of the present invention, which may, inter alia, inhibit the proliferation of lymphocytes that accompanies the autoimmune pathology. A patient with a disorder which results in the induction of inflammation may be treated using the methods and compositions of the present invention to prevent, inhibit, or lessen the induction of the inflammatory cascade and protect against the damage resulting from activation of T cells, mast cells, eosinophils, basophils, and neutrophils. The methods and compositions of the present invention can also be useful for preventing, inhibiting, or lessening the induction and tissue damage that may be caused by, for example, cytokines and chemokines, interleukins, interferons, lymphokines, tumor necrosis factors, tumor necrosis factor-like cytokines, lymphotoxin-α, lymphotoxin-β, interferon-α, interferon-β, macrophage inflammatory proteins, granulocyte monocyte colony stimulating factor, interleukins (including, but not limited to, interleukin-1, interleukin-2, interleukin-6, interleukin-12, interleukin-15, interleukin-18), OX40, CD27, CD30, CD40 or CD137 ligands, Fas-Fas ligand, 4-1BBL, endothelial monocyte activating protein or any fragments, family members, or derivatives thereof, including pharmaceutically acceptable salts thereof.

As used herein, the term "cancer" describes a disease state in which a carcinogenic agent or agents causes the transformation of a healthy cell into an abnormal cell, which is followed by an invasion of adjacent tissues by these abnormal cells, and which may be followed by lymphatic, cerebral spinal fluid, or blood-borne spread of these abnormal cells to regional lymph nodes and/or distant sites, i.e., metastasis.

As used herein, the term "tumor" or "growth" means increased tissue mass, which includes greater cell numbers as a result of faster cell division and/or slower rates of cell death. Tumors may be malignant or non-malignant cancers.

As used herein, the phrases "treating cancer" and "treatment of cancer" mean to inhibit the replication of cancer cells, inhibit the spread of cancer, decrease tumor size, lessen or reduce the number of cancerous cells in the body, or ameliorate or alleviate the symptoms of the disease caused by the cancer. The treatment is considered therapeutic if there is a decrease in mortality and/or morbidity, or a decrease in disease burden manifest by reduced numbers of malignant cells in the body.

As used herein, the phrases "preventing cancer" and "prevention of cancer" mean to prevent the occurrence or recurrence of the disease state of cancer. As such, a treatment that impedes, inhibits, or interferes with metastasis, tumor growth, or cancer proliferation has preventive activity.

As used herein, the phrase "antisense oligomer" means an antisense oligonucleotide or an analogue or derivative thereof, and refers to a range of chemical species that recognize polynucleotide target sequences through Watson-and-Crick hydrogen bonding interactions with the nucleotide bases of the target sequences. The target sequences may be RNA or DNA, and may be single-stranded or double-stranded. Target molecules include, but are not limited to, pre-mRNA, mRNA, and DNA.

As used herein, the phrase "bcl-2 gene expression" refers to transcription of the bcl-2 gene which produces bcl-2 pre-mRNA, bcl-2 mRNA, and/or bcl-2 protein, which encompasses portions of the bcl-2 polypeptide.

As used herein, the phrase "therapeutics" or "therapeutic agents" refers to any molecules, compounds or treatments that assist in the treatment of a disease. As such, a cancer therapeutic is a molecule, compound or treatment protocol that aids in the treatment of tumors or cancer. The treatment protocol may include, but is not limited to, radiation therapy, dietary therapy, physical therapy, and psychological therapy.

As used herein, the phrase "chemoagent" or "anti-cancer agent" or "anti-tumor agent" or "cancer therapeutic" refers to any molecule, compound or treatment that assists in the treatment of tumors or cancer.

As used herein, the phrase "low dose" or "reduced dose" refers to a dose that is below the normally administered range, i.e., below the standard dose as suggested by the *Physicians' Desk Reference, 54th Edition* (2000) or a similar reference. Such a lower or reduced dose may be sufficient to inhibit cell proliferation, or demonstrates ameliorative effects in a human, or demonstrates efficacy with fewer side effects as compared to standard cancer treatments. Normal dose ranges used for particular therapeutic agents and standard cancer treatments employed for specific diseases can be found, for example, in the *Physicians' Desk Reference, 54th Edition* (2000) or in *Cancer: Principles & Practice of Oncology*, DeVita, Jr., Hellman, and Rosenberg (eds.) 2nd edition, Philadelphia, Pa.: J. B. Lippincott Co., 1985.

As used herein, the phrase "reduced toxicity" refers to the reduced side effects and toxicities observed in connection with administering the oligomers of the present invention and other cancer therapeutics for shorter duration and/or at lower dosages when compared to other treatment protocols and dosage formulations, including the standard treatment protocols and dosage formulations as described in the *Physicians' Desk Reference*, 54th *Edition* (2000) or in *Cancer: Principles & Practice of Oncology*, DeVita, Jr., Hellman, and Rosenberg (eds.) 2nd edition, Philadelphia, Pa.: J. B. Lippincott Co., 1985.

As used herein, the phrase "treatment cycle" or "cycle" refers to a period during which a single therapeutic or sequence of therapeutics is administered. In one embodiment encompassing the use of high doses of bcl-2 antisense oligomer and CRE decoy (or hybrids thereof), in combination with a standard dose of a cancer therapeutic, the preferred period length of time for one treatment cycle is less than 14 days. The present invention contemplates at least one treatment cycle, generally preferably more than one cycle. In some instances, one treatment cycle may be desired, such as, for example, in the case where a significant therapeutic effect is obtained after one treatment cycle.

As used herein, the phrase "pharmaceutically acceptable carrier" refers to a carrier medium that does not interfere with the effectiveness of the biological activity of the active ingredient. Said carrier medium is essentially chemically inert and nontoxic.

As used herein, the phrase "pharmaceutically acceptable" means approved by a regulatory agency of the Federal government or a state government, or listed in the U.S. Pharmacopeia or other generally recognized pharmacopeia for use in animals, and more particularly for use in humans.

As used herein, the term "carrier" refers to a diluent, adjuvant, excipient, or vehicle with which the therapeutic is administered. Such carriers can be sterile liquids, such as saline solutions in water, or oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The carrier, if desired, can also contain minor amounts of wetting or emulsifying agents, or pH buffering agents. These pharmaceutical compositions can take the form of solutions, suspensions, emulsion, tablets, pills, capsules, powders, sustained-release formulations and the like. The composition can be formulated as a suppository, with traditional binders and carriers such as triglycerides. Examples of suitable pharmaceutical carriers are described in *Remington's Pharmaceutical Sciences* by E. W. Martin. Examples of suitable pharmaceutical carriers are a variety of cationic polyamines and lipids, including, but not limited to N-(1(2,3-dioleyloxy)propyl)-N,N,N-trimethylammonium chloride (DOTMA) and diolesylphosphotidylethanolamine (DOPE). Liposomes are also suitable carriers for the oligomers of the invention. Such pharmaceutical compositions should contain a therapeutically effective amount of the compound, together with a suitable amount of carrier so as to provide the form for proper administration to the patient. The formulation should suit the mode of administration.

As used herein, the phrase "pharmaceutically acceptable salts" refers to salts prepared from pharmaceutically acceptable, essentially nontoxic, acids and bases, including inorganic and organic acids and bases. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

4. DETAILED DESCRIPTION OF THE INVENTION

The present invention provides methods for preventing or treating a cell-proliferative related disorder comprising administering to a subject in need of such treatment a combination of a bcl-2 antisense oligomer and a cyclic AMP response element (CRE) decoy oligomer. The present invention also provides pharmaceutical compositions for the administration of a bcl-2 antisense oligomer in combination with a CRE decoy oligomer.

The present invention also is directed to hybrid oligomers comprising a CRE oligomer and a sequence that hybridizes to a bcl-2 pre-mRNA or mRNA (bcl-2 antisense/CRE decoy hybrid or "bcl-2/CRE hybrid oligomer"). The invention is further directed to methods comprising administering to a subject in need of such treatment a bcl-2/CRE hybrid oligomer for preventing or treating a cell-proliferative related disorder. The invention also provides pharmaceutical compositions comprising a CRE hybrid oligomer. The invention further provides drug delivery and therapeutic regimens for prophylactic and therapeutic treatments.

The present invention also provides methods for treating or preventing a cell-proliferative related disorder comprising administering to a subject in need of such treatment a bcl-2 antisense oligomer and a CRE decoy oligomer, and one or more additional cancer therapeutic agents. Additionally, the invention provides methods comprising administering, alone or in combination with one or more additional cancer therapeutic agents, a bcl-2/CRE hybrid oligomer to prevent or treat cancer. Such cancer therapeutics include one or more molecules, compounds or treatments that have anti-cancer activity. Examples of contemplated cancer therapeutics include biologicals (e.g., cytokines), chemicals (e.g., chemoagents), and therapeutic treatments (e.g., irradiation treatment).

Combinations of these treatments may offer a potency benefit. For example, targeting, in one treatment cycle, both a protein that binds a CRE enhancer (e.g., a transcription factor) and a bcl-2 pre-mRNA or mRNA can have greater therapeutic effect than targeting either CRE-binding proteins or bcl-2 RNA alone. Furthermore, the combined impact of modulating CRE-driven transcription and bcl-2 expression can potentiate the therapeutic effect of other anti-cancer treatments.

4.1 Bcl-2 Antisense Oligomer

The present invention encompasses an oligomer that hybridizes to a bcl-2 mRNA or pre-mRNA. Also encompassed are oligomers that hybridizes to a portion (e.g., at least 10, 11, 12, 13, 14, 15, 16, 17, 18, 19 or 20 consecutive nucleotides) of a bcl-2 mRNA or pre-mRNA. Such oligomers may be capable of decreasing translation of the bcl-2 message. Accordingly, the invention contemplates use of one or more bcl-2 antisense oligomers, or a derivative, analog or fragment thereof. As used herein, the term "derivative" refers to any pharmaceutically acceptable homolog, analogue, or fragment, which retains the ability to bind to a bcl-2 mRNA or a portion (e.g., at least 10, 11, 12, 13, 14, 15, 16, 17, 18, 19 or 20 consecutive nucleotides) thereof. Antisense oligomers suitable for use in the invention include oligomers which range in size from 5 to 10, 10 to 20, 20 to 50, 50 to 75, 75 to 100, or 101 to 1000 bases in length; preferably 10 to 40 bases in length; more preferably 12 to 25 bases in length; most preferably 18 bases in length.

In one embodiment, the bcl-2 antisense sequence comprises at least 10 bases or at least 10 consecutive bases that are complementary to a bcl-2 pre-mRNA or bcl-2 mRNA. In one embodiment, the bcl-2antisenseoligomer is 10, 11, 12, 13, 14, 15, 16, 17, 18, 19, 20, 21, 22, 23, 24, or 25 bases in length. In another embodiment, the bcl-2 antisense sequence comprises the sequence 5'-TCTCCCAGCG-3' (SEQ ID NO:35). In another embodiment, the bcl-2 antisense sequence comprises the sequence 5'-TCTCCCAGCGT-3' (SEQ ID NO:41). In another embodiment, the bcl-2 antisense sequence comprises the sequence 5'-TCTCCAGCGTG-3' (SEQ ID NO:44). In another embodiment, the bcl-2 antisense sequence comprises the sequence 5'-TCTCCCAGCGTGC-3' (SEQ ID NO:45). In another embodiment, the bcl-2 antisense sequence comprises the sequence 5'-TCTCCCAGCGTGCG-3' (SEQ ID NO:46:). In another embodiment, the bcl-2 antisense sequence comprises the sequence 5'-TCTCCCAGCGTGCGC-3' (SEQ ID NO:47). In another embodiment, the bcl-2 antisense sequence comprises the sequence 5'-TCTCCCAGCGTGCGCC-3 (SEQ ID NO:48). In yet another embodiment, the bcl-2 antisense sequence comprises the sequence 5'-TCTCCAGCGTGCGCCA-3' (SEQ ID NO:49). In another embodiment, the bcl-2 oligomer comprises the sequence: 5'-TCTCCCAGCGTGCGCCAT-3' (SEQ ID NO:17; also known as G3139 or Genasense™). In other embodiments, the bcl-2 oligomer comprises CAGCGTGCGCCATCCT-TCCC (SEQ ID NO: 1), CTTTTCCTCTGGGAAGGATG-GCGCACGCTGGGAGA (SEQ ID NO :2), GATGCAC-CTACCCAGCCTCC (SEQ ID NO:3), ACGGGGTACGGAGGCTGGGTAGGTGCATCGGT (SEQ II) NO:4), ACAAAGGCATCCTGCAGTTG (SEQ ID NO:5), CCCCCAACTGCAGGATGCCTTTGTG-GAACTGTACGG (SEQ ID NO:6), GGGAAGGATGGCG-CACGCTG (SEQ ID NO:7), CGCGTGCGACCCTCTTG (SEQ ID NO:8), TACCGCGTGCGACCCTC (SEQ ID NO:9), TCCTACCGCGTGCGACC (SEQ ID NO:10), CCT-TCCTACCGCGTGCG (SEQ ID NO:11), GACCCTTC-CTACCGCGT (SEQ ID NO: 12), GGAGACCCTFC-CTACCG (SEQ ID NO: 13), GCGGCGGCAGCGCGG (SEQ ID NO:14), CGGCGGGGCGACGGA (SEQ ID NO:15), CGGGAGCGCGGGCGGGC (SEQ ID NO:16), TCTCCCAGCGTGCGCCAT (SEQ ID NO:17), TGCACT-CACGCTCGGCCT (SEQ ID NO:18), GCGCG-GCGGGCGGGCGGGCA (SEQ ID NO:26), GGGCGGAG-GCCGGCCGGCGG (SEQ ID NO:27), AGCGGCGGCGGCGGCAGCGC (SEQ ID NO:28), or GGGCCGGGAAGGGCGCCCGC (SEQ ID NO:29), which correspond to SEQ ID NOS. 1 to 18 and 24 to 29, respectively, in U.S. Pat. No. 5,831,066 which is incorporated herein by reference in its entirety.

The target sequences may be RNA or DNA, and may be single-stranded or double-stranded. Target molecules include, but are not limited to, pre-mRNA, mRNA, and DNA. In one embodiment, the target molecule is a single-stranded RNA. In a further embodiment, the target molecule is mRNA. In a preferred embodiment, the target molecule is bcl-2 pre-mRNA or bcl-2 mRNA. In a specific embodiment, the antisense oligomers hybridize to a portion anywhere along a bcl-2 pre-mRNA or mRNA. The antisense oligomers are preferably selected from those oligomers which hybridize to the translation initiation site, donor splicing site, acceptor splicing site, sites for transportation, or sites for degradation of the bcl-2 pre-mRNA or mRNA.

In one embodiment, the bcl-2 antisense oligomer hybridizes to a sequence in the coding region of a bcl-2 mRNA. In a further embodiment, the oligomer can decrease expression of a bcl-2 gene product. In another embodiment, the bcl-2 antisense oligomer hybridizes to a sequence found in a non-coding region of a bcl-2 mRNA or pre-mRNA, e.g., a sequence found in the upstream regulatory region required for translation of a bcl-2 message. In a further embodiment, the oligomer can decrease the expression of a bcl-2 gene product.

In one embodiment, the bcl-2 antisense oligomer is substantially complementary to a portion of a bcl-2 pre-mRNA or mRNA, or to a portion of a pre-mRNA or mRNA that is related to bcl-2. In a preferred embodiment, the bcl-2 antisense oligomer hybridizes to a portion of the translation-initiation site of the pre-mRNA coding strand. In a more preferred embodiment, the bcl-2 antisense oligomer hybridizes to a portion of the pre-mRNA coding strand that comprises the translation-initiation site of the human bcl-2 gene. More preferably, the bcl-2 antisense oligomer comprises a TAC sequence which is complementary to the AUG initiation sequence of a bcl-2 pre-mRNA or RNA.

In another embodiment, the bcl-2 antisense oligomer hybridizes to a portion of the splice donor site of the pre-mRNA coding strand for the human bcl-2 gene. Preferably, this nucleotide comprises a CA sequence, which is complementary to the GT splice donor sequence of a bcl-2 gene, and preferably further comprises flanking portions of 5 to 50 bases, more preferably from about 10 to 20 bases, which hybridizes to portions of a bcl-2 gene coding strand flanking said splice donor site.

In yet another embodiment, the bcl-2 antisense oligomer hybridizes to a portion of the splice acceptor site of the pre-mRNA coding strand for the human bcl-2 gene. Preferably, this nucleotide comprises a TC sequence, which is complementary to the AG splice acceptor sequence of a bcl-2 gene, and preferably further comprises flanking portions of 5 to 50 bases, more preferably from about 10 to 20 bases, which hybridizes to portions of a bcl-2 gene coding strand flanking said splice acceptor site. In another embodiment, the bcl-2 antisense oligomer hybridizes to portions of the pre-mRNA or mRNA involved in splicing, transport or degradation.

One of average skill in the art can recognize that antisense oligomers suitable for use in the invention may also be substantially complementary to other sites along a bcl-2 pre-mRNA or mRNA, and can form hybrids. The skilled artisan will also appreciate that antisense oligomers that hybridize to a portion of a bcl-2 pre-mRNA or mRNA, but whose sequence does not commonly occur in transcripts from unrelated genes, are preferable so as to maintain treatment specificity.

In one embodiment, the sequence that hybridizes to a bcl-2 pre-mRNA or mRNA, hybridizes under high stringency, i.e., conditions for hybridization and washing under which nucleotide sequences, which are at least 60% (preferably 65%, 70%, 75% or greater) identical to each other, typically remain hybridized to each other. Such stringent conditions are known to those skilled in the art, and can be found, for example, in *Current Protocols in Molecular Biology*, John Wiley & Sons, N.Y. (1989), 6.3.1–6.3.6, which describes aqueous and non-aqueous methods, either of which can be used. Another example of stringent hybridization conditions is hybridization of the nucleotide sequences in 6×sodium chloride/sodium citrate (SSC) at about 45° C., followed by 0.2×SSC, 0.1% SDS at 50–65° C. Particularly preferred stringency conditions, (which should be used if the practitioner is uncertain of the stringency conditions to be applied to determine whether the complementarity of a nucleotide sequence is within the scope of the embodiment of the invention), are hybridization in 6×sodium chloride/sodium citrate (SSC) at about 45° C., followed by one or more washes in 0.2×SSC, 0.1% SDS at 50° C. Another example of stringent hybridization conditions are hybridization in 6×sodium chloride/sodium citrate (SSC) at about 45° C., followed by one or more washes in 0.2×SSC, 0.1% SDS at 55° C. A further example of stringent hybridization conditions are hybridization in 6×sodium chloride/sodium citrate (SSC) at about 45° C., followed by one or more washes in 0.2×SSC, 0.1% SDS at 60° C. Preferably, stringent hybridization conditions are hybridization in 6×sodium chloride/sodium citrate (SSC) at about 45° C., followed by one or more washes in 0.2×SSC, 0.1% SDS at 65° C. Another preferred example of stringent hybridization condition is 0.5M sodium phosphate, 7% SDS at 65° C., followed by one or more washes at 0.2×SSC, 1% SDS at 65° C.

In another embodiment, the sequence that hybridizes to a bcl-2 pre-mRNA or mRNA, hybridizes under low stringency conditions, which conditions are known to those skilled in the art (see, e.g., Sambrook et al. *Molecular Cloning: A Laboratory Manual* 2$^{nd}$ Ed., Cold Spring Harbor Laboratory Press, NY, (1989), 9.47–9.55). For example, low stringency hybridization conditions can be achieved by incubating the nucleotide sequences in 6×sodium chloride/sodium citrate (SSC) at about 45° C. overnight, followed by one or more washes in either 0.2×SSC, 0.1% SDS at room temperature, or 0.2×SSC, 0.1% SDS at 37° C., or 0.2×SSC, 0.1% SDS at 42° C., or 2×SSC, 0.1% SDS at 50° C.

Examples of bcl-2 antisense oligomers that may be used in accordance with the present invention are described in detail in U.S. patent application Ser. No. 08/217,082, now U.S. Pat. No. 5,734,033; U.S. patent application Ser. No. 08/465,485, now U.S. Pat. No. 5,831,066; and U.S. patent application Ser. No. 09/080,285, now U.S. Pat. No. 6,040,181, each of which is incorporated herein by reference in its entirety.

The design of the sequence of a bcl-2 antisense oligomer can also be determined by empirical testing and assessment of activity in an art-recognized model system or clinical effectiveness, regardless of its degree of sequence homology to, or hybridization with, a bcl-2 gene, bcl-2 pre-mRNA, bcl-2 mRNA, or bcl-2 related nucleotide sequences. One of ordinary skill in the art will appreciate that bcl-2 antisense oligomers having, for example, less sequence homology, greater or fewer modified nucleotides, or longer or shorter lengths, compared to those of the preferred embodiments, but which nevertheless demonstrate effectiveness in clinical treatments, are also within the scope of the invention.

The antisense oligomers may be RNA or DNA, or derivatives thereof. The particular form of antisense oligomer may affect the oligomer's pharmacokinetic parameters such as bioavailability, metabolism, half-life, etc. As such, the invention contemplates antisense oligomer derivatives having properties that improve cellular uptake, enhance nuclease resistance, improve binding to the target sequence, or increase cleavage or degradation of the target sequence. The antisense oligomers may contain bases comprising, for example, phosphodiesters, phosphorothioates or methylphosphonates, among others. In one embodiment, the antisense oligomers, instead, can be mixed oligomers. Such oligomers may possess modifications which comprise, but are not limited to, 2-O'-alkyl or 2-O'-halo sugar modifications, backbone modifications (e.g. methylphosphonate, phosphorodithioate, phosphordithioate, formacetal, 3'-thioformacetal, sulfone, sulfamate, nitroxide backbone, morpholino derivatives and peptide nucleic acid (PNA) derivatives), or derivatives wherein the base moieties have been modified (Egholm et al., 1992, *Peptide Nucleic Acids (PNA)-Oligomer Analogues With An Achiral Peptide Backbone;* Nielsen et al., 1993, "Peptide nucleic acids (PNAs): potential antisense and anti-gone agents", Anticancer Drug Des 8:53–63). Mixed oligomers may comprise any combination of modified bases. In another embodiment, antisense oligomers comprise conjugates of the oligomers and derivatives thereof (Goodchild, 1990, "Conjugates of oligomers and modified oligomers: a review of their synthesis and properties", Bioconjug. Chem. 1(3):165–87).

For in vivo therapeutic use, several types of nucleoside derivatives are available. A phosphorothioate derivative of the oligomers of the invention can be useful for in vivo therapeutic use, in part due to the greater resistance to degradation. In one embodiment, the bcl-2 antisense oligomer comprises phosphorothioate bases. In another embodiment, the bcl-2 antisense oligomer contains at least one phosphorothioate linkage. In another embodiment, the bcl-2 antisense oligomer contains at least three phosphorothioate linkages. In a further embodiment, the bcl-2 antisense oligomer contains at least three consecutive phosphorothioate linkages. In yet another embodiment, the bcl-2 antisense oligomer is comprised entirely of phosphorothioate linkages. Methods for preparing oligonucleotide derivatives are known in the art. See, e.g., Stein et al., 1988, "Physicochemical properties of phosphorothioate oligodeoxynucleotides", Nucl. Acids Res., 16:3209–21 (phosphorothioate); Blake et al., 1985, "Inhibition of rabbit globin mRNA translation by sequence-specific oligodeoxyribonucleotides", Biochemistry 24:6132–38 (methylphosphonate); Morvan et al., 1986, "alpha-DNA. I. Synthesis, characterization by high field 1H-NMR, and base-pairing properties of the unnatural hexadeoxyribonucleotide alpha-[d(CpCpTpTpCpC)] with its complement beta-[d(GpGpApApGpG)]. Nucl. Acids Res. 14:5019–32 (alphadeoxynucleotides)", Nucl. Acids Res. 14:5019–32 (alphadeoxynucleotides); Monia et al., 1993, "Evaluation of 2'-modified oligonucleotides containing 2' deoxy gaps as antisense inhibitors of gene expression", J. Biol. Chem. 268:14514–22 (2'-O-methyl-ribonucleosides); Asseline et al., 1984, "Nucleic acid-binding molecules with high affinity and base sequence specificity: intercalating agents covalently linked to oligodeoxynucleotides", Proc. Natl Acad. Sci. USA 81:3297–3301 (acridine); Knorre et al., 1985, "Biochemie 67:783–9; Vlassov et al., 1986, "Nucleic acid-binding molecules with high affinity and base sequence specificity: intercalating agents covalently linked to oligodeoxynucleotides", Nucl. Acids Res. 14:4065–76 (N-2-chlorocethylamine and phenazine); Webb et al., 1986, "Hybridization triggered cross-linking of deoxyoligonucleotides", Nucl. Acids Res. 14:7661–74 (5-methyl-$N^4$-$N^4$-ethanocytosine); Boutorin et al., 1984, "FEBS Letters 172:43–6 (Fe-ethylenediamine tetraacetic acid (EDTA) and analogues); Chi-Hong et al., 1986, Proc. Natl. Acad. Sci. USA 83:7147–51 (5-glycylamido-1, 10-o-phenanthroline); and Chu et al., 1985, "Nonenzymatic sequence-specific cleavage of single-stranded DNA", Proc. Natl. Acad. Sci. USA 82:963–7 (diethylenetriaamine-pentaacetic acid (DTPA) derivatives).

4.2 CRE Decoy Oligomer

The invention contemplates the use of one or more CRE decoy oligomers, or its derivatives, analogues or fragments thereof. Preferably, a CRE decoy oligomer is an oligomer which will bind to transcription factors capable of binding a CRE (e.g., CREB), and thereby hinder or prevent binding of the transcription factor to a CRE enhancer. In one embodiment, the CRE decoy oligomer comprises a CRE sequence. In a preferred embodiment, the CRE decoy oligomer comprises a CRE consensus sequence, e.g., TGACGTCA, or a derivative or analogue of a CRE consensus sequence that retains the ability to compete with CRE enhancers for binding to transcription factors. In one embodiment, the CRE decoy oligomer comprises two CRE sequences, which may or may not be attached by a linker (Table 1, constructs 1a and 1b). In a further embodiment, a first CRE sequence is linked to a second CRE sequence by one or more bases. In a particular embodiment, the CRE decoy oligomer comprises a doublet or a triplet of a CRE consensus sequence, e.g., TGACGTCA, or an analog or derivative thereof. In a specific embodiment, the CRE decoy oligomer is a 24-mer consisting of a triplet of TGACGTCA or an analog or derivative thereof.

The CRE decoy oligomer may comprise at least two copies of the CRE consensus sequence, TGACGTCA, which may or may not be attached by a linker (Table 1, constructs 2a and 2b). The linker may be a nucleotide or a polynucleotide. In another embodiment, the linker comprises the sequence, TGACGTCA. In another embodiment, the linker may comprise one or more adenine residues. In another embodiment, the linker may comprise one or more cytosine residues. In another embodiment, the linker may comprise one or more guanine residues. In yet another embodiment, the linker may comprise one or more thymidine residues. In a particular embodiment, the linker comprises 1, 2, 3, or 4 thymidine bases. In another embodiment, the linker comprises any nucleoside base, including modified nucleosides. In another embodiment, the linker comprises a thymidine residue. In another embodiment, the linker comprises two thymidine residues. In another embodiment, the linker comprises three thymidine residues. In another embodiment, the linker comprises four thymidine residues. In yet another embodiment, the linker comprises at least five thymidine residues.

In one embodiment, the linker is a nucleotide sequence of 1, 2, 3, 4, 5, 6, 7, 8, 9, 10, 11, 12, 13, 14, 15, 16, 17, or 18 bases in length. In another embodiment, the linker sequence is 1–4, 5–8, 9–12, or 13–18 bases in length.

Alternatively, the linker may be a non-nucleotide chemical moiety. In one embodiment, the linker is absent. In a further embodiment, the CRE decoy oligomer comprises a double-strande molecule of the sequence 5'-TGACGTCA-3'.

In a preferred embodiment, the CRE sequence is present as a double-stranded helix. In one preferred embodiment, the CRE decoy oligomer contains at least two CRE consensus sequences, or analogs or derivatives thereof, which may be separated by a linker of sufficient length to allow for duplex formation.

Also contemplated by the invention are CRE sequences that vary from the consensus sequence, by means of base substitutions, deletions or additions. Furthermore, CRE sequences corresponding to identified native CRE enhancers, or CRE-like sequences, and variants thereof, are also encompassed by the present invention. For example, use of native CRE enhancer sequences, or variants thereof obtained by, for example, base substitutions, deletions or additions, can be useful for targeting specific CRE-driven transcriptional units, or particular classes of CRE-driven transcriptional units. In order to obtain variants of CRE or CRE-like sequences by base substitution, preferably, conservative amino acid substitutions are made at one or more predicted non-essential amino acid residues. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. The amino acids also can be grouped as (1) acidic=aspartate, glutamate; (2) basic=lysine, arginine histidine, (3) aliphatic=glycine, alanine, valine, leucine, isoleucine, serine, threonine, with serine and threonine optionally grouped separately as aliphatic-hydroxyl; (4) aromatic=phenylalanine, tyrosine, tryptophan; (5) amide=asparagine, glutamine; and (6) sulfur-containing=cysteine and methionine. (See, e.g., Biochemistry, 4th ed., L. Stryer (ed.), W H Freeman and Co. 1995).

CRE decoy oligomers suitable for use, and contemplated by the invention, include oligomers which range in size from 16 to 50 bases in length; preferably 17 to 40 bases in length; more preferably from 18 to 38 bases in length; more preferably from 19 to 36 bases in length; and most preferably from 20 to 34 bases in length. In one embodiment, the CRE decoy oligomer is 16 bases in length. In another embodiment, the oligomer is 24 bases in length. In another embodiment, the oligomer is 17–20, 21–24, 25–30, 31–34, 35–40, 41–44, or 45–50 bases in length.

The CRE decoy oligomers may be DNA or RNA, or derivatives or analogues thereof. The CRE sequences may contain bases (e.g. nucleosides or nucleotides) comprising, for example, phosphodiesters, phosphorothioates or methylphosphonates, among others. The invention contemplates a CRE decoy oligomer comprised of any modified backbone that is recognized by a CRE-associated protein. The CRE oligomers, instead, can be mixed oligomers, which may comprise any combination of modified bases. Such oligomers may possess modifications which comprise, but are not limited to, hexitol nucleic acids, G-clamp heterocycle modifications, 2-O'-alkyl or 2-O'-halo sugar modifications, backbone modifications (e.g., methylphosphonate, phosphorodithioate, phosphordithioate, formacetal, 3'-thioformacetal, sulfone, sulfamate, nitroxide backbone, morpholino derivatives and peptide nucleic acid (PNA) derivatives), or derivatives wherein the base moieties have been modified (Egholm et al., 1992, *Peptide Nucleic Acids (PNA)-Oligonucleotide Analogues With An Achiral Peptide Backbone*). In another embodiment, the CRE oligomers comprise conjugates of the oligonucleotides and derivatives thereof (Goodchild, 1990, "Conjugates of oligonucleotides and modified oligonucleotides: a review of their synthesis and properties", Bioconjug. Chem. 1(3):165–87).

For in vivo therapeutic use, a phosphorothioate derivative of the CRE decoy oligomer can be useful, at least partly because of greater resistance to degradation. In one embodiment, the CRE decoy oligomer comprises phosphorothioate bases. In another embodiment, the CRE decoy oligomer contains at least one phosphorothioate linkage. In another embodiment, the CRE decoy oligomer contains at least three phosphorothioate linkages. In yet another embodiment, the CRE decoy oligomer contains at least three consecutive phosphorothioate linkages. In yet another embodiment, the CRE decoy oligomer is comprised entirely of phosphorothioate linkages. Methods for preparing oligonucleotide derivatives are known in the art. See, e.g., Stein et al., 1988, Nucl. Acids Res., 16:3209–21 (phosphorothioate); Blake et al., 1985, Biochemistry 24:6132–38 (methylphosphonate); Morvan et al., 1986, Nucl. Acids Res. 14:5019–32 (alphadeoxynucleotides); Monia et al., 1993, "Evaluation of 2'-modified oligonucleotides containing 2' deoxy gaps as antisense inhibitors of gene expression", J. Biol. Chem. 268:14514–22 (2'-O-methyl-ribonucleosides); Asseline et al., 1984, Proc. Natl Acad. Sci. USA 81:3297–3301 (acridine); Knorre et al., 1985, Biochemie 67:783–9; Vlassov et al., 1986, Nucl. Acids Res. 14:4065–76 (N-2-chlorocethylamine and phenazine); Webb et al., 1986, Nucl. Acids Res. 14:7661–74 (5-methyl-$N^4$-$N^4$-ethanocytosine); Boutorin et al., 1984, FEBS Letters 172:43–6 (Fe-ethylenediamine tetraacetic acid (EDTA) and analogues); Chi-Hong et al., 1986, Proc. Natl. Acad. Sci. USA 83:7147–51 (5-glycylamido-1, 10-o-phenanthroline); and Chu et al., 1985, Proc. Natl. Acad. Sci. USA 82:963–7 (diethylenetriaamine-pentaacetic acid (DTPA) derivatives).

CRE decoy oligomers that may be used in accordance with the present invention include, but are not limited to, oligomers (some which bind to cAMP) having non-native sequences, consensus sequences (e.g., 5'-TGACGTCA-3'), as well as CREs, CRE-like sequences, and putative CREs that are associated with native genes. Several examples of sequences useful in the present invention are provided in Section 3.1 for illustrative purposes. Further examples of CRE decoy oligomers that may be used in accordance with the present invention are described in detail in U.S. patent application Ser. No. 08/977,643, now U.S. Pat. No. 6,060, 310, which is incorporated herein by reference in its entirety.

The design of the sequence of a CRE decoy oligomer can also be determined by empirical testing and assessment of activity in an art-recognized model system or clinical effectiveness.

4.3 Bcl-2/CRE Hybrid Oligomer

The invention provides a hybrid oligomer with dual activities, which include the ability to hybridize to a bcl-2 pre-mRNA or bcl-2 mRNA, optionally resulting in reduced expression of the bcl-2 gene product, and the ability to compete with CRE or CRE-like enhancers for binding to transcription factors, optionally modulating the transcriptional activities of sequence-specific DNA-binding proteins. In a particular embodiment, the bcl-2/CRE hybrid oligomer comprises a CRE sequence and a sequence that hybridizes to a bcl-2 mRNA or bcl-2 pre-mRNA ("bcl-2 sequence"). In one embodiment, the bcl-2/CRE hybrid oligomer comprises two CRE sequences which are linked by a linker comprising a sequence that hybridizes to a bcl-2 pre-mRNA or bcl-2 mRNA ("bcl-2 sequence"), such that the bcl-2 sequence is flanked on both ends by a CRE sequence (Table 1, construct 1c). In another embodiment, the bcl-sequence is flanked only on one end by a CRE sequence (Table 9, construct 1d). For example, a linker can be a bcl-2 antisense sequence repeated 2, 3, 4, 5, 6, 7, 8, 9 or 10 times, optionally in tandem.

The hybrid oligomers of the present invention comprise a bcl-2 antisense oligomer and a CRE decoy oligomer. In accordance with the present invention, the two oligomers are attached in such a way to permit each oligomer to be able to retain their respective activity, i.e., the ability to decrease expression of a bcl-2 gene produce and the ability to compete with CRE enhancers for binding to transcription factors. However, in accordance with the present invention, it is not necessary that each individual hybrid oligomer be able to perform both activities simultaneously.

In a preferred embodiment, the hybrid oligomers contain at least two CRE sequences, such that they are able to form a duplex and at least one bcl-2 antisense oligomer. The hybrid oligomers of the invention may be constructed in such a way that the two CRE sequences are attached by a linker sequence, so that a hairpin structure is formed when the two CRE sequences hybridize to each other and the bcl-2 sequence is attached to either the 5' or 3' end of the hairpin structure (Table 1, construct 1e). In a preferred embodiment, the bcl-2 antisense oligomer is incorporated into the linker sequence joining the two CRE sequences. In such an embodiment, when the two CRE sequences hybridize to each other, a stem loop structure is formed such that the stem comprises a CRE decoy oligomer and the loop comprises a bcl-2 antisense oligomer.

CRE decoy oligomers suitable for use in a hybrid oligomer include oligomers comprising CRE nucleotide sequences which range in size from 16 to 50 bases in length; preferably 17 to 40 bases in length; more preferably from 18 to 38 bases in length; more preferably from 19 to 36 bases in length; and most preferably from 20 to 34 bases in length. In one embodiment, the CRE nucleotide sequence is 16 bases in length. In another embodiment, the CRE nucleotide sequence is 24 bases in length. In another embodiment, the CRE nucleotide sequence is 17 to 20, 21 to 24, 25 to 30, 31 to 34, 35 to 40, 41 to 44, or 45 to 50 bases in length. In a particular embodiment, the CRE nucleotide sequence comprises a CRE consensus sequence, TGACGTCA. In a specific embodiment, the CRE decoy oligomer comprises a repeated sequence of TGACGTCA.

Bcl-2 antisense sequences suitable for use in a bcl-2/CRE hybrid oligomer include oligomers which range in size from 5 to 9, 10 to 19, 20 to 49, 50 to 74, 75 to 100, or 101 to 1000 bases in length; preferably 10 to 40 bases in length; more preferably 15 to 25 bases in length; most preferably 18 bases in length. In one embodiment, the bcl-2 antisense oligomer is 10, 11, 12, 13, 14, 15, 16, 17, 18, 19, 20, 21, 22, 23, 24, or 25 bases in length. In one embodiment, the bcl-2 antisense sequence comprises at least 10 bases that are complementary to the bcl-2 pre-mRNA or mRNA. In a further embodiment, the bcl-2 antisense sequence comprises at least 10 consecutive bases that are complementary to the bcl-2 pre-mRNA or mRNA. In one specific embodiment, the bcl-2 oligomer comprises the sequence 5'-TCTCCCAGCG-3' (SEQ ID NO:35). In another specific embodiment, the bcl-2 oligomer comprises the sequence 5'-CGTGCGCCAT-3' (SEQ ID NO:50). In another specific embodiment, the bcl-2 oligomer comprises the sequence 5'-CCAGCGTG-3', In another specific embodiment, the bcl-2 oligomer comprises the sequence 5'-CCAGCGTGC-3', In another specific embodiment, the bcl-2 oligomer comprises the sequence 5'-CCAGCGTGCG-3' (SEQ ID NO:51). In another specific embodiment, the bcl-2 oligomer comprises the sequence 5'-CCCAGCGTCGC-3' (SEQ ID NO:52). In another specific embodiment, the bcl-2 oligomer comprises the sequence 5'-TCCCAGCGTGCGCC-3' (SEQ ID NO:53). In another specific embodiment, the bcl-2 oligomer comprises the sequence 5'-CTCCCAGCGTGCGCCA-3' (SEQ ID NO:54). In yet another specific embodiment, the bcl-2 oligomer comprises the sequence 5'-TCTCCCAGCGTGCGCCAT-3' (SEQ ID NO:17; also known as G3139).

In one embodiment, the sequence that hybridizes to a bcl-2 pre-mRNA or mRNA, hybridizes under high stringency, i.e., conditions for hybridization and washing under which nucleotide sequences, which are at least 60% (preferably 65%, 70%, 75% or greater) identical to each other, typically remain hybridized to each other. Such stringent conditions are known to those skilled in the art, and can be found, for example, in Current Protocols in Molecular Biology, John Wiley & Sons, N.Y. (1989), 6.3.1–6.3.6, which describes aqueous and non-aqueous methods, either of which can be used. Another example of stringent hybridization conditions is hybridization of the nucleotide sequences in 6× sodium chloride/sodium citrate (SSC) at about 45° C., followed by 0.2×SSC, 0.1% SDS at 50–65° C. Particularly preferred stringency conditions, (which should be used if the practitioner is uncertain of the stringency conditions to be applied to determine whether the complementarity of a nucleotide sequence is within the scope of the embodiment of the invention), are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions are hybridization in 6× sodium chloride/sodium citrate (SSC) at about 45° C., followed by one or more washes in 0.2×SSC, 0.1% SDS at 60° C. Preferably, stringent hybridization conditions are hybridization in 6× sodium chloride/sodium citrate (SSC) at about 45° C., followed by one or more washes in 0.2×SSC, 0.1% SDS at 65° C. Another preferred example of stringent hybridization condition is 0.5M sodium phosphate, 7% SDS at 65° C., followed by one or more washes at 0.2×SSC, 1% SDS at 65° C.

In another embodiment, the sequence that hybridizes to a bcl-2 pre-mRNA or mRNA, hybridizes under low stringency conditions, which conditions are known to those skilled in the art (see, e.g., Sambrook et al. *Molecular Cloning: A Laboratory Manual* 2$^{nd}$ Ed., Cold Spring Harbor Laboratory Press, NY, (1989), 9.47–9.55). For example, low stringency hybridization conditions can be achieved by incubating the nucleotide sequences in 6× sodium chloride/sodium citrate (SSC) at about 45° C. overnight, followed by one or more washes in either 0.2×SSC, 0.1% SDS at room temperature, or 0.2×SSC, 0.1% SDS at 37° C., or 0.2×SSC, 0.1% SDS at 42° C., or 2×SSC, 0.1% SDS at 50° C.

The bcl-2/CRE hybrid oligomer can be approximately 50, 60, 70, 80, 90, 100, 500 or 1000 bases in length. The bcl-2/CRE hybrid oligomer preferably ranges in size from 25 to 50 bases in length; more preferably 28 to 40 bases in length; more preferably 30 to 36 bases in length. In one embodiment, the hybrid oligomer is 30, 31, 32, 33, 34, 35 or 36 bases in length.

The oligomers of the invention may contain modified nucleotides including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, β-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, β-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Additionally, the oligomers of the invention may possess modifications which comprise, but are not limited to, hexitol nucleic acids, G-clamp heterocycle modifications, 2-O'-alkyl or 2-O'-halo sugar modifications, backbone modifications (e.g., methylphosphonate, phosphorothioate, phosphorodithioate, phosphordithioate, formacetal, 3'-thioformacetal, sulfone, sulfamate, nitroxide backbone, morpholino derivatives and peptide nucleic acid (PNA) derivatives), or derivatives wherein the base moieties have been modified (Egholm, et al., 1992, *Peptide Nucleic Acids (PNA)-Oligonucleotide Analogues With An Achiral Peptide Backbone;* Hyrup et al., 1996, "Peptide nucleic acids (PNA): synthesis, properties and potential applications", Bioorganic & Medicinal Chemistry 4(1): 5–23; Verma and Eckstein, 1998, "Modified oligonucleotides: synthesis and strategy for users", Annu Rev Biochem. 67:99–134). In another embodiment, the oligomers comprise conjugates of the oligonucleotides and derivatives thereof (Goodchild, 1990, "Conjugates of oligonucleotides and modified oligonucleotides: a review of their synthesis and properties", Bioconjug. Chem. 1(3):165–87).

In another embodiment, the oligomers of the invention comprise an α-anomeric nucleic acid molecule. An α-anomeric nucleic acid molecule forms specific double-stranded hybrids with complementary RNA in which, contrary to the usual β-units, the strands run parallel to each other (Gaultier et al., 1987, Nucleic Acids Res. 15:6625–6641). In yet another embodiment, the oligomers of the invention comprise a 2'-o-methylribonucleotide (Inoue et al., 1987, "Synthesis and hybridization studies on two complementary nona(2'-O-methyl)ribonucleotides", Nucleic Acids Res. 15:6131–6148) or a chimeric RNA-DNA analogue (Inoue et al., 1987, "Sequence-dependent hydrolysis of RNA using modified oligonucleotide splints and RNase H", FEBS Lett. 215:327–330).

The bcl-2/CRE hybrid oligomer can be linked, for example, to peptides (e.g., to target host cell receptors in vivo), or to agents that aid in transport across the cell membrane (See, e.g., Letsinger et al., 1989, "Cholesteryl-conjugated oligonucleotides: synthesis, properties, and activity as inhibitors of replication of human immunodeficiency virus in cell culture", Proc. Natl. Acad. Sci. USA 86:6553–6556; Lemaitre et al., 1987, "Specific antiviral activity of a poly(L-lysine)-conjugated oligodeoxyribonucleotide sequence complementary to vesicular stomatitis virus N protein mRNA initiation site", Proc. Natl. Acad. Sci. USA 84:648–652; PCT International Publication No. WO 88/09810) or that aid in transport across the blood-brain barrier (See, e.g., PCT International Publication No. WO 89/10134). In addition, the oligomers of the invention can be modified with hybridization-triggered cleavage agents (See, e.g., Krol et al., 1988, "Modulation of eukaryotic gene expression by complementary RNA or DNA sequences", BioTechniques 6:958–976) or intercalating agents (See, e.g., Zon, 1988, "Oligonucleotide analogues as potential chemotherapeutic agents", Pharm. Res. 5:539–549).

In one embodiment, the hybrid oligomer comprises a bcl-2 antisense oligomer and a CRE sequence. In a specific embodiment, the CRE sequence of the hybrid oligomer comprises the CRE consensus sequence, TGACGTCA. In another specific embodiment, the hybrid oligomer further comprises the bcl-2 antisense sequence, TCTCCCAGC. In yet another embodiment In another embodiment, the bcl-2/CRE hybrid oligomer comprises a CRE consensus sequence, which is attached to a linker sequence, which is attached to another CRE consensus sequence. In a particular embodiment, the bcl-2/CRE hybrid oligomer comprises a CRE consensus sequence, which is attached to the 5' end of the linker, and a CRE consensus sequence, which is attached to the linker's 3' end (Table 1, construct 2a). In a further embodiment, the linker sequence comprises a sequence that hybridizes to a bcl-2 pre-mRNA or bcl-2 mRNA (Table 1, construct 2b). In a particular embodiment, the linker sequence comprises at least 5, 6, 7, 8, 9, 10, 11, 12, 13, 14, 15, 16, 17 or 18 consecutive bases complementary to a bcl-2 mRNA or bcl-2 pre-mRNA. In another particular embodiment, the linker region comprises repeated bcl-2 antisense sequences, optionally in tandem. In a specific embodiment, the hybrid oligomer comprises the sequence 5'-TGACGTCATCTC-CCAGCGTGCGCCATTGACGTCA-3' (SEQ ID NO:33). In another specific embodiment, the hybrid oligomer comprises the sequence 5'-TGACGTCATCTCCCAGCGT-GCGCCATTCTCCCAGCGTGCGCCATTGACGTCA-3' (SEQ ID NO:34).

In another embodiment, the hybrid oligomer comprises a bcl-2 antisense oligomer attached to a CRE decoy oligomer. The bcl-2 antisense oligomer and CRE decoy oligomer can be attached by means of a linker, which may comprise a non-nucleic acid moiety. The bcl-2 antisense oligomer and CRE decoy oligomer may also be attached enzymatically or by crosslinking. Many methods for linking to a nucleic acid are known in the art (See, e.g., Catalog of TriLink BioTechnologies, Inc. 2001). Linkers may be placed at the 3' end of the nucleic acid molecule, at the 5' end of the molecule, and/or internally. Linkers useful for producing hybrid oligomers of the present invention include, but are not limited to, quenchers (e.g., TAMRA, DABCYL, QSYT™, DABSYL, DABCYL), amino linkers, thiol linkers, propyl spacers, triethylene glycol spacers, tetraethylene glycol spacers, hexaethylene glycol spacers, and terminal phosphates. Linker lengths can be varied. Moreover, a linker can be further modified, for example, to produce specialized linkers such as the amino linkers, monomethoxytritylaminohexyl phosphoramidite and monomethoxytritylaminododecyl phosphoramidite.

CRE decoy oligomers suitable to be attached to a bcl-2 antisense oligomer may comprise a CRE consensus sequence, which is attached to a linker, which is attached to another CRE consensus sequence. In one embodiment, the CRE decoy oligomer comprises a CRE consensus sequence, which is attached to the 5' end of the linker, and a CRE consensus sequence, which is attached to the 3' end of the linker (Table 1, construct 2a). In a further embodiment, the linker comprises a CRE consensus sequence (Table 1, construct 3a). In another embodiment, the linker comprises at least one adenine base. In another embodiment, the linker comprises at least one cytosine base. In another embodiment, the linker comprises at least one guanine base. In another embodiment, the linker comprises at least one thymidine base. In a further embodiment, the linker comprises a series of thymidine residues. In a specific embodiment, the linker is TTT (Table 1, construct 3b). In another specific embodiment, the linker is TT (Table 1, construct 3c). In yet another specific embodiment, the linker is T (Table 1, construct 3d). In one embodiment, the bcl-2 antisense oligomer is attached to the linker of the CRE decoy oligomer (Table 1, construct 4). In a further embodiment, the bcl-2 antisense oligomer can be attached indirectly to the CRE decoy oligomer by intervening bases.

In another embodiment, the hybrid oligomer comprises a CRE oligomer comprising the CRE consensus sequence, TGACGTCA, at least two of which are linked by a nucleotide sequence comprising a bcl-2 antisense sequence (Table 1, construct 2b). In a further embodiment, the bcl-2 antisense sequence comprises at least 10 bases that are complementary to a bcl-2 pre-mRNA or mRNA. In a particular embodiment, the bcl-2 antisense sequence comprises the sequence 5'-TCTCCCAGCGTGCGCCAT-3' (SEQ ID NO: 17). In another particular embodiment, the bcl-2 antisense sequence comprises the sequence 5'-TCTCCCAGCGTGCGCCA-3' (SEQ ID NO:49). In another particular embodiment, the bcl-2 antisense sequence comprises the sequence 5'-TCTCCAGCGTGCGCC-3' (SEQ ID NO:48). In another particular embodiment, the bcl-2 antisense sequence comprises the sequence 5'-TCTCCCAGCGTGCGC-3' (SEQ ID NO:47). In another particular embodiment, the bcl-2 antisense sequence comprises the sequence 5'-TCTCCCAGCGTGCG-3' (SEQ ID NO:35). In another particular embodiment, the bcl-2 antisense sequence comprises the sequence 5'-TCTCCCAGCGTGC-3' (SEQ ID NO:45). In another particular embodiment, the bcl-2 antisense sequence comprises the sequence 5'-TCTCCCAGCGTG-3' (SEQ ID NO:44). In another particular embodiment, the bcl-2 antisense sequence comprises the sequence 5'-CTCCCAGCGT-3' (SEQ ID NO:55). In yet another particular embodiment, the bcl-2 antisense sequence comprises the sequence 5'-TCTCCCAGCG-3' (SEQ ID NO:56). In a specific embodiment, the hybrid oligomer comprises the sequence 5'-TGACGTCATCTCCCAGCGTGCGCC-3' (SEQ ID NO:57). In another specific embodiment, the phosphorothioate hybrid oligomer comprises the sequence 5'-TGACGTCATCTCCCAGCGTGCGCCATTGACGTCA-3' (SEQ ID NO:33).

of T cells, mast cells, eosinophils, basophils, and neutrophils. In yet another example, the methods and compositions of the present invention may be used to prevent cell proliferation associated with angiogenesis, including, but not limited to, cells of the vasculature and cells of the tissues secreting the angiogenic factors.

The methods and compositions of the present invention can also be useful for preventing, inhibiting, or lessening the induction and tissue damage that may be caused by, for example, cytokines, chemokines, interleukins, interferons, lymphokines, tumor necrosis factors, tumor necrosis factor-like cytokines, lymphotoxin-α, lymphotoxin-β, interferon-α, interferon-β, macrophage inflammatory proteins, granulocyte monocyte colony stimulating factor, interleukins (including, but not limited to, interleukin-1, interleukin-2, interleukin-6, interleukin-12, interleukin-15, interleukin-18), OX40, CD27, CD30, CD40 or CD137 ligands, Fas-Fas ligand, 4-1 BBL, endothelial monocyte activating protein or any fragments, family members, or derivatives thereof, including pharmaceutically acceptable salts thereof.

The effective dose of bcl-2 antisense oligomer and/or CRE decoy to be administered during a treatment cycle ranges from about 0.01 to 0.1, 0.1 to 1, or 1 to 10 mg/kg/day. Accordingly, the administered dose can be, for example, 0.01, 0.025, 0.05, 0.075, 1, 2, 3, 4, 5, 6, 7, 8, 9 or 10 mg/kg/day. The dose of bcl-2 antisense oligomer and/or

TABLE 1

| Construct | |
|---|---|
| 1a | CRE sequence - CRE sequence |
| 1b | CRE sequence - linker - CRE sequence |
| 1c | CRE sequence - bcl-2 sequence - CRE sequence |
| 1d | bcl-2 sequence - CRE sequence - CRE sequence |
| 1e | CRE sequence - linker - CRE sequence - bcl-2 sequence |
| 2a | CRE consensus sequence - linker - CRE consensus sequence |
| 2b | CRE consensus sequence - bcl-2 sequence - CRE consensus sequence |
| 3a | CRE consensus sequence - CRE consensus sequence - CRE consensus sequence |
| 3b | CRE consensus sequence - TTT - CRE consensus sequence |
| 3c | CRE consensus sequence - TT - CRE consensus sequence |
| 3d | CRE consensus sequence - T - CRE consensus sequence |
| 4 | bcl-2 sequence<br>\|<br>CRE consensus sequence - linker - CRE consensus sequence |

4.4 Methods of Use of Bcl-2 Antisense Oligomer and CRE Decoy Oligomer

The invention provides a method for the use of a CRE decoy which is administered prior to, subsequently, or concurrently with one or more bcl-2 antisense oligomers, for the prevention or treatment of a cell-proliferative disorder, particularly cancer. Cell-proliferative disorders encompasses diseases involving cell division induced by, or concomitant with, for example, bacterial infections, viral infections, inflammation, inflammatory conditions (e.g., anaphylaxis, allergy, arthritis, asthma, microbial infection, parasitic infection), and autoimmune disorders. For example, a patient with an autoimmune disease may be treated using the methods and compositions of the present invention, which may, inter alia, inhibit the proliferation of lymphocytes that accompanies the autoimmune pathology. In another example, a patient with a disorder which results in inflammation may be treated using the methods and compositions of the present invention to prevent, inhibit, or lessen the induction of the inflammatory response, and thereby protect against damage resulting from the activation CRE decoy to be administered can be dependent on the mode of administration. For example, intravenous administration of a bcl-2 antisense oligomer and/or CRE decoy would likely result in a significantly higher full body dose than a full body dose resulting from a local implant containing a pharmaceutical composition comprising bcl-2 antisense oligomer and/or CRE decoy. In one embodiment, a bcl-2 antisense oligomer and/or CRE decoy is administered subcutaneously at a dose of 0.01 to 10 mg/kg/day; more preferably at a dose of 4 to 9 mg/kg/day; most preferably at a dose of 5 to 7 mg/kg/day. In another embodiment, a bcl-2 antisense oligomer and/or CRE decoy is administered intravenously at a dose of 0.01 to 10 mg/kg/day; more preferably at a dose of 4 to 9 mg/kg/day; most preferably at a dose of 5 to 7 mg/kg/day. In yet another embodiment, a bcl-2 antisense oligomer and/or CRE decoy is administered locally at a dose of 0.01 to 10 mg/kg/day; preferably at a dose of 0.01 to 0.1; more preferably at a dose of 1 to 5 mg/kg/day. It will be evident to one skilled in the art that local administrations can result in lower total body doses. For example, local administration methods such as intratumor administration, intraocular injection, or implantation, can produce locally high concentrations of bcl-2 antisense oligomer and/or CRE decoy, but represent a relatively low dose with respect to total body weight. Thus, in such cases, local administration of a bcl-2 antisense oligomer and/or CRE decoy is contemplated to result in a total body dose of about 0.01 to 5 mg/kg/day.

In another embodiment, a particularly high dose of bcl-2 antisense oligomer and/or CRE decoy, which ranges from about 10 to 20, 20 to 30, or 30 to 50 mg/kg/day, is administered during a treatment cycle. In another embodiment, a particularly high dose of bcl-2 antisense oligomer and/or CRE decoy, which ranges from about 10 to 14, 15 to 20, 21 to 25, 26 to 30, 31 to 35, 36 to 40, 41 to 45 or 46 to 50 mg/kg/day, is administered during a treatment cycle. In a specific embodiment, a bcl-2 antisense oligomer and/or CRE decoy oligomer is administered to a subject in need of such treatment at a dose of 10, 11, 12, 13, 14, 15, 16, 17, 18, 19, or 20 mg/kg/day.

Moreover, the effective dose of a particular bcl-2 antisense oligomer and/or CRE decoy may depend on additional factors, including the type of cancer, the disease state or stage of disease, the oligomer's toxicity, the oligomer's rate of uptake by cancer cells, as well as the weight, age, and health of the individual to whom the oligomer is to be administered. Because of the many factors present in vivo that may interfere with the action or biological activity of a bcl-2 antisense oligomer and/or CRE decoy, one of ordinary skill in the art can appreciate that an effective amount of a bcl-2 antisense oligomer and/or CRE decoy may vary for each individual.

In another embodiment, a bcl-2 antisense oligomer and/or CRE decoy is at a dose which results in circulating plasma concentrations of the bcl-2 antisense oligomer and/or CRE decoy which is at least 20, 25, 30, 35, 40, 45, or 50 nM (nanomolar); preferably at least 30 nM. As will be apparent to the skilled artisan, lower or higher plasma concentrations of the bcl-2 antisense oligomer and/or CRE decoy may be preferred depending on the mode of administration. For example, plasma concentrations of the bcl-2 antisense oligomer and/or CRE decoy of at least 30 nM can be appropriate in connection with intravenous, subcutaneous, intramuscular, controlled release, and oral administration methods, to name a few. In another example, relatively low circulating plasma levels of the bcl-2 antisense oligomer and/or CRE decoy can be desirable, however, when using local administration methods such as, for example, intratumor administration, intraocular administration, or implantation, which nevertheless can produce locally high, clinically effective concentrations of bcl-2 antisense oligomer and CRE decoy.

In yet another embodiment, the circulating plasma concentration of at least 20, 25, 30, 35, 40, 45, or 50 nM (nanomolar), preferably at least 30 nM, of the bcl-2 antisense oligomer and/or CRE decoy is achieved about 1, 2, 3, 4, 5, 6, 7, 8, 9 or 10 hours after the administration of the bcl-2 antisense oligomer and/or CRE decoy. In yet another embodiment, the circulating plasma concentration of at least 20, 25, 30, 35, 40, 45, or 50 nM (nanomolar), preferably at least 30 nM, of the bcl-2 antisense oligomer and/or CRE decoy is achieved in about 36 to 48 hours, preferably 24 to 35 hours, more preferably in 12 to 24 hours; most preferably in under 12 hours.

In a specific embodiment, the dose of a bcl-2 antisense oligomer and/or CRE decoy is a high dose. In one embodiment, the circulating plasma concentration of the bcl-2 antisense oligomer and/or CRE decoy is at least 30 nM.

In another embodiment, the circulating level of bcl-2 antisense oligomer and/or CRE decoy is 1 µM to 10 µM. In yet another embodiment, the circulating level of bcl-2 antisense oligomer and/or CRE decoy is 1, 2, 3, 4, 5, 6, 7, 8, 9 or 10 µM. In yet another embodiment, the circulating level of bcl-2 antisense oligomer and/or CRE decoy of 1 µM to 10 µM is achieved in about 36 to 48 hours, preferably 24 to 35 hours, more preferably in 12 to 24 hours; most preferably in under 12 hours.

The high dose may be achieved by several administrations per cycle. Alternatively, the high dose may be administered in a single bolus administration. A single administration of a high dose may result in circulating plasma levels of bcl-2 antisense oligomer and/or CRE decoy that are transiently much higher than 30 nM. Moreover, single administrations of particularly high doses of a bcl-2 antisense oligomer and/or CRE decoy may result in a circulating plasma concentration of bcl-2 antisense oligomer and/or CRE decoy of 1 µM to 10 µM in much less 12 hours, even in less than one hour.

Additionally, the dose of a bcl-2 antisense oligomer and/or CRE decoy may vary according to the particular bcl-2 antisense oligomer or CRE decoy used. The dose employed is likely to reflect a balancing of considerations, among which are stability, localization, cellular uptake, and toxicity of a particular bcl-2 antisense oligomer or CRE decoy. For example, a particular chemically modified bcl-2 antisense oligomer or CRE decoy may exhibit greater resistance to degradation, or may exhibit higher affinity for the target nucleic acid or protein, or may exhibit increased uptake by the cell or cell nucleus; all of which may permit the use of low doses. In another example, a particular chemically modified bcl-2 antisense oligomer or CRE decoy may exhibit lower toxicity than other oligomers, and therefore can be used at high doses. Thus, for a given bcl-2 antisense oligomer and/or CRE decoy, an appropriate dose to administer can be relatively high or relatively low. Appropriate doses or ranges of dosages would be appreciated by the skilled artisan, and the invention contemplates the continued assessment of optimal treatment schedules for particular species of bcl-2 antisense oligomers or CRE decoy oligomers. The daily dose can be administered in one or more treatments.

Other factors to be considered in determining an effective dose of a bcl-2 antisense oligomer or CRE decoy include the effect of administering a bcl-2 antisense oligomer in combination with a CRE decoy oligomer, or whether the oligomers will be administered in combination with other therapeutics. In such cases, the relative toxicity of the bcl-2 antisense oligomer plus CRE decoy oligomer combination therapy and/or the additional therapeutics may indicate the use of a bcl-2 antisense oligomer and/or CRE decoy at low doses. Alternatively, treatment with a high dose of bcl-2 antisense oligomer and/or CRE decoy can result in combination therapies with reduced doses of additional therapeutics. In a specific embodiment, treatment with a particularly high dose of bcl-2 antisense oligomer and/or CRE decoy can result in combination therapies with greatly reduced doses of additional cancer therapeutics. For example, treatment of a patient with 10, 20, 30, 40, or 50 mg/kg/day of a bcl-2 antisense oligomer and/or CRE decoy can further increase the sensitivity of a subject to additional cancer therapeutics. In such cases, the particularly high dose of bcl-2 antisense oligomer and/or CRE decoy is combined with, for example, a greatly shortened radiotherapy schedule. In another example, the particularly high dose of a bcl-2 antisense oligomer and/or CRE decoy produces significant enhancement of the potency of additional cancer therapeutic agents.

Additionally, the particularly high doses of bcl-2 antisense oligomer and/or CRE decoy may further shorten the period of administration of a therapeutically effective amount of bcl-2 antisense oligomer, CRE decoy and/or additional cancer therapeutic agent, such that the length of a treatment cycle is much shorter than 14 days.

In one embodiment, the bcl-2 antisense oligomer comprises a sequence of which at least 10 bases, optionally consecutive, are complementary to the bcl-2 pre-mRNA or mRNA. In one specific embodiment, the bcl-2 oligomer comprises the sequence 5'-TCTCCCAGCG-3' (SEQ ID NO:35). In another specific embodiment, the bcl-2 oligomer comprises the sequence 5'-CGTGCGCCAT-3' (SEQ ID NO:50). In another specific embodiment, the bcl-2 oligomer comprises the sequence 5'-CCAGCGTGCG-3' (SEQ ID NO:51). In another specific embodiment, the bcl-2 oligomer comprises the sequence 5'-CCCAGCGTGCGC-3' (SEQ ID NO:52). In another specific embodiment, the bcl-2 oligomer comprises the sequence 5'-TCCCAGCGTGCGCC-3' (SEQ ID NO:53). In another specific embodiment, the bcl-2 oligomer comprises the sequence 5'-CTCCCAGCGT-GCGCCA-3' (SEQ ID NO:54). In yet another specific embodiment, the bcl-2 oligomer comprises the sequence 5'-TCTCCCAGCGTGCGCCAT-3' (SEQ ID NO:17; also known as G3139).

In one embodiment, a CRE decoy oligomer comprises a CRE, CRE-like, or putative CRE sequence, or a variant thereof. In one embodiment, the CRE decoy oligomer comprises a CRE consensus sequence. In a further embodiment, the CRE decoy oligomer comprises the CRE consensus sequence, TGACGTCA. In another embodiment, the CRE decoy oligomer comprises at least two copies of the CRE consensus sequence, TGACGTCA. In yet another embodiment, the CRE decoy oligomer comprises the CRE consensus sequence, TGACGTCA, at least two of which are linked by a nucleotide sequence.

In another embodiment, a CRE decoy comprises a double-stranded molecule comprising two oligomers having a CRE, CRE-like, or putative CRE sequence, or a variant thereof. In one embodiment, the CRE decoy comprises a CRE consensus sequence. In a further embodiment, the CRE decoy oligomer comprises the CRE consensus sequence, TGACGTCA. The two oligomers may be linked or crosslinked.

In a specific embodiment, an 18-base phosphorothioate bcl-2 antisense oligomer of the sequence 5'-TCTC-CCAGCGTGCGCCAT-3' (SEQ ID NO:17), which is complementary to the first six codons of the bcl-2 mRNA and hybridizes to the respective target RNA bases, is administered in combination with a 24-base phosphorothioate CRE decoy of the sequence 5'-TGACGTCATGACGTCAT-GACGTCA-3' (SEQ ID NO:36).

In one embodiment, bcl-2 antisense oligomer and/or CRE decoy is administered for 2 to 13 days at a dose of 0.01 to 10 mg/kg/day. In a specific embodiment, bcl-2 antisense oligomer and/or CRE decoy is administered for 2 to 3, 4 to 5, 6 to 7, 8 to 9, 10 to 11, or 12 to 13 days at a dose of 0.01 to 1, 1 to 2, 3 to 4, 5 to 6, 6 to 7, 7 to 8, or 9 to 10 mg/kg/day; more preferably at a dose of 4 to 9 mg/kg/day, and most preferably at a dose of 5 to 7 mg/kg/day. In another embodiment, bcl-2 antisense oligomer and/or CRE decoy is administered at said dose for 3 to 9 days. In yet another embodiment, bcl-2 antisense oligomer and/or CRE decoy is administered at said dose for 4 to 7 days. In a preferred embodiment, bcl-2 antisense oligomer and/or CRE decoy is administered at said dose for 5 to 6 days. In a most preferred embodiment, bcl-2 antisense oligomer and/or CRE decoy is administered at a dose of 5 to 7 mg/kg/day for 5 to 6 days. The invention contemplates other preferred treatment regimens depending on the particular bcl-2 antisense oligomer and/or CRE decoy to be used, or depending on the particular mode of administration, or depending on whether the bcl-2 antisense oligomer and/or CRE decoy is administered in combination with additional cancer therapeutic agents. The daily dose can be administered in one or more treatments.

In another embodiment, bcl-2 antisense oligomer and/or CRE decoy is administered at a particularly high dose of about 10 to 50 mg/kg/day. In a specific embodiment, bcl-2 antisense oligomer and/or CRE decoy is administered at a particularly high dose of about 10 to 15, 16 to 20, 21 to 25, 26 to 30, 31 to 35, 36 to 40, 41 to 45, or 46 to 50 mg/kg/day. In a further embodiment, bcl-2 antisense oligomer and/or CRE decoy is administered at said dose for 1 to 10 days. In yet another embodiment, bcl-2 antisense oligomer and/or CRE decoy is administered at said dose for 2 to 7 days. In a yet another embodiment, bcl-2 antisense oligomer and/or CRE decoy is administered at said dose for 3 to 4 days. In a preferred embodiment, bcl-2 antisense oligomer and/or CRE decoy is administered at a dose of 10 to 15, 16 to 20, 21 to 25, 26 to 30, 31 to 35, 36 to 40, 41 to 45, or 46 to 50 mg/kg/day for minimum of one day. The invention contemplates other preferred treatment regimens depending on the particular bcl-2 antisense oligomer and/or CRE decoy to be used, or depending on the particular mode of administration, or depending on whether the bcl-2 antisense oligomer and/or CRE decoy is administered in combination with additional cancer therapeutic agents. The daily dose can be administered in one or more treatments.

In one embodiment, the invention provides a method for the use of a CRE decoy and a bcl-2 antisense oligomer, which is administered for the prevention or treatment of colon cancer.

In another embodiment, the invention provides a method for the use of a CRE decoy and a bcl-2 antisense oligomer, which is administered for the prevention and treatment of hepatitis B virus infection.

In another embodiment, the invention provides a method for the use of a CRE decoy and a bcl-2 antisense oligomer to inhibit the growth of cancer cells in vitro comprising contacting the cancer cells with a bcl-2 antisense oligomer and a CRE decoy oligomer.

4.5 Methods of Use of bcl-2/CRE Hybrid Oligomer

The present invention provides hybrid oligomers comprising a cyclic AMP response element (CRE) sequence and a sequence that hybridizes to the bcl-2 pre-mRNA or mRNA. These compositions can be useful as research and diagnostic tools. The hybrid oligomers can be used broadly to study CRE-sensitive gene expression and/or bcl-2 related cell function, including but not limited to, cell survival, morphology, proliferation, and/or differentiation. For example, many identified genes that have CRE enhancers 5' of the coding region, or elsewhere in the transcriptional unit, are amenable to functional studies in which the gene's transcription is influenced by a hybrid oligomer. Similarly, the effects of a hybrid oligomer of the present invention on cells that express the bcl-2 gene can be studied in vitro.

Interestingly, the bcl-2/CRE hybrid oligomers can be used to study biological events that are affected by both Bcl-2 and CRE-dependent expression. For example, CRE-driven transcription and Bcl-2 protein expression both can affect apoptotic processes. Therefore, a bcl-2/CRE hybrid oligomer may serve as a valuable research tool in the study of apoptosis-related cellular events.

In particular, uncontrolled cell growth or cell division can be studied in vitro using the bcl-2/CRE hybrid oligomers. The hybrid oligomers of the invention can be tested on several cancer cell lines, for instance, to characterize the sensitivity of different tumor types to CRE decoy plus bcl-2 antisense treatment. Similar studies can be performed on non-cancer cell lines, correlating the effects of a bcl-2/CRE hybrid oligomers with the growth characteristics of each cell line, for example. Using the hybrid oligomers of the invention, studies of cell/tissue growth or organization can be performed on tissue cultures or tissue explants as well.

The hybrid oligomers of the present invention also can be used for screening candidate transcription factors or other molecules (e.g., gene regulatory proteins) found in, or associated with, transcriptional complexes. For example, CRE enhancer sequences corresponding to native sequences, consensus sequences, or variants thereof, can comprise a bcl-2/CRE hybrid oligomer, which can be useful for screening and identifying transcription factors and associated proteins that bind, directly or indirectly, to specific CRE sequences. These screening assays can be performed in cell-free or cell-based systems. For example, a protein array of transcription factors or proteins similar to transcription factors, can be screened with a hybrid oligomer of the invention, and the binding detected to identify the protein(s) that recognize a specific CRE sequence. The relative strength of binding can be determined by standard binding assays. The efficacy of transcriptional activation or repression can be determined using constructs comprising the hybrid oligomer and a standard reporter sequence.

The hybrid oligomers of the invention, or fragments thereof, can also be used as polynucleotide reagents. For example, hybridization of the oligomers to nucleic acid samples can be used to identify gene regions associated with genetic disease. For example, the nucleic acid sequence of a hybrid oligomer can be used to map the location of the gene on a chromosome, which is a primary means of correlating specific genes associated with a particular disease state. Several methods for gene mapping are known in the art (See, e.g., D'Eustachio et al., 1983, Science 220:919–924; Fan et al., 1990, Proc. Natl. Acad. Sci. USA 87:6223–6227; Verma et al., *Human Chromosomes: A Manual of Basic Techniques*, Pergamon Press, New York, 1988).

The nucleic acid sequence of the hybrid oligomers of the invention may be used to identify mutations and polymorphisms, which can be useful for determining the source of a biological sample.

The hybrid oligomers of the present invention also can be used for diagnostic assays. Accordingly, one aspect of the present invention relates to diagnostic assays of a biological sample (e.g., serum, blood, cells, tissue) to determine the presence and levels of bcl-2 expression and/or to determine the expression of factors associated with CRE enhancers. Such assays can have prognostic or predictive value to a subject in need of diagnosis, prophylaxis, or treatment. To illustrate, a transcription factor that binds to a particular CRE enhancer sequence can be identified in a biological sample by: obtaining a biological sample from a test subject, contacting the biological sample with a hybrid oligomer of the invention, detecting the binding between the transcription factor and the hybrid oligomer, and isolating the transcription factor.

The bcl-2/CRE hybrid oligomers can also be useful for general research purposes. For example, sites of localization of the bcl-2 mRNA or pre-mRNA can be determined by in situ hybridization. Additionally, the localization of the hybrid oligomers bound to transcription factors that recognize a CRE sequence, can be determined by electron microscopy. Similarly, the bcl-2/CRE hybrid oligomers can be labeled and monitored in live cells or tissue by, for example, epifluorescence. In studies of RNA expression the hybrid oligomers of the present invention can be used as probes for northern blot analysis. Furthermore, in studies of protein-nucleic acid interactions, the hybrid oligomers of the present invention can be used as probes in gel-shift assays.

The invention also provides methods for use of an oligomer comprising a hybrid of CRE and bcl-2 antisense oligonucleotide sequences for the prevention or treatment of cell-proliferative related disorders. Such a disorder encompasses diseases involving cell division induced by, or concomitant with, for example, bacterial infections, viral infections, inflammation, inflammatory conditions (e.g., anaphylaxis, allergy, arthritis, asthma, microbial infection, parasitic infection), and autoimmune disorders. For example, a patient with an autoimmune disease may be treated using the methods and compositions of the present invention, which may, inter alia, inhibit the proliferation of lymphocytes that accompanies the autoimmune pathology. In another example, a patient with a disorder which results in inflammation may be treated using the methods and compositions of the present invention to prevent, inhibit, or lessen the induction of the inflammatory response, and thereby protect against damage resulting from the activation of T cells, mast cells, eosinophils, basophils, and neutrophils. In yet another example, the methods and compositions of the present invention may be used to prevent cell proliferation associated with angiogenesis, including, but not limited to, cells of the vasculature and cells of the tissues secreting the angiogenic factors.

The methods and compositions of the present invention can also be useful for preventing, inhibiting, or lessening the induction and tissue damage that may be caused by, for example, cytokines, chemokines, interleukins, interferons, lymphokines, tumor necrosis factors, tumor necrosis factor-like cytokines, lymphotoxin-$\alpha$, lymphotoxin-$\beta$, interferon-$\alpha$, interferon-$\beta$, macrophage inflammatory proteins, granulocyte monocyte colony stimulating factor, interleukins (including, but not limited to, interleukin-1, interleukin-2, interleukin-6, interleukin-12, interleukin-15, interleukin-18), OX40, CD27, CD30, CD40 or CD137 ligands, Fas-Fas ligand, 4-1BBL, endothelial monocyte activating protein or any fragments, family members, or derivatives thereof, including pharmaceutically acceptable salts thereof.

In one embodiment, the bcl-2/CRE hybrid oligomer is administered alone. In another embodiment, the bcl-2/CRE hybrid oligomer is administered in combination with a bcl-2 antisense oligomer. In another embodiment, a bcl-2/CRE hybrid oligomer is administered in combination with a CRE decoy. In another embodiment, a bcl-2/CRE hybrid oligomer is administered in combination with a cancer therapeutic agent. In yet another embodiment, a bcl-2/CRE hybrid oligomer is administered in combination with a bcl-2 antisense oligomer, CRE decoy oligomer, and/or other cancer therapeutic agent.

The invention contemplates the use of one of more bcl-2/CRE hybrid oligomers. In one embodiment, the bcl-2/CRE hybrid oligomer is administered prior to, subsequently, or concurrently with one or more bcl-2 antisense oligomers, CRE decoy oligomers, and/or additional cancer therapeutic agents for the prevention or treatment of cancer.

The effective dose of bcl-2/CRE hybrid oligomer to be administered during a treatment cycle ranges from about 0.01 to 0.1, 0.1 to 1, or 1 to 10 mg/kg/day. Accordingly, the administered dose can be, for example, 0.01, 0.025, 0.05, 0.075, 1, 2, 3, 4, 5, 6, 7, 8, 9 or 10 mg/kg/day. The dose of bcl-2/CRE hybrid oligomer to be administered can be dependent on the mode of administration. For example, intravenous administration of a bcl-2/CRE hybrid oligomer would likely result in a significantly higher full body dose than a full body dose resulting from a local implant containing a pharmaceutical composition comprising bcl-2/CRE hybrid oligomer. In one embodiment, a bcl-2/CRE hybrid oligomer is administered subcutaneously at a dose of 0.01 to 10 mg/kg/day; more preferably at a dose of 4 to 9 mg/kg/day; most preferably at a dose of 5 to 7 mg/kg/day. In another embodiment, a bcl-2/CRE hybrid oligomer is administered intravenously at a dose of 0.01 to 10 mg/kg/day; more preferably at a dose of 4 to 9 mg/kg/day; most preferably at a dose of 5 to 7 mg/kg/day. In yet another embodiment, a bcl-2/CRE hybrid oligomer is administered locally at a dose of 0.01 to 10 mg/kg/day; preferably at a dose of 0.01 to 0.1; more preferably at a dose of 1 to 5 mg/kg/day. It will be evident to one skilled in the art that local administrations can result in lower total body doses. For example, local administration methods such as intratumor administration, intraocular injection, or implantation, can produce locally high concentrations of bcl-2/CRE hybrid oligomer, but represent a relatively low dose with respect to total body weight. Thus, in such cases, local administration of a bcl-2/CRE hybrid oligomer is contemplated to result in a total body dose of about 0.01 to 5 mg/kg/day.

In another embodiment, a particularly high dose of bcl-2/CRE hybrid oligomer, which ranges from about 10 to 20, 20 to 30, or 30 to 50 mg/kg/day, is administered during a treatment cycle.

Moreover, the effective dose of a particular bcl-2/CRE hybrid oligomer may depend on additional factors, including the type of cancer, the disease state or stage of disease, the oligomer's toxicity, the oligomer's rate of uptake by cancer cells, as well as the weight, age, and health of the individual to whom the oligomer is to be administered. Because of the many factors present in vivo that may interfere with the action or biological activity of a bcl-2/CRE hybrid oligomer, one of ordinary skill in the art can appreciate that an effective amount of a bcl-2/CRE hybrid oligomer may vary for each individual.

In another embodiment, a bcl-2/CRE hybrid oligomer is at a dose which results in circulating plasma concentrations of the bcl-2/CRE hybrid oligomer which is at least 30 nM (nanomolar). As will be apparent to the skilled artisan, lower or higher plasma concentrations of the bcl-2/CRE hybrid oligomer may be preferred depending on the mode of administration. For example, plasma concentrations of the bcl-2/CRE hybrid oligomer of at least 30 nM can be appropriate in connection with intravenous, subcutaneous, intramuscular, controlled release, and oral administration methods, to name a few. In another example, relatively low circulating plasma levels of the bcl-2/CRE hybrid oligomer can be desirable, however, when using local administration methods such as, for example, intratumor administration, intraocular administration, or implantation, which nevertheless can produce locally high, clinically effective concentrations of bcl-2/CRE hybrid oligomer.

In yet another embodiment, the circulating plasma concentration of at least 30 nM (nanomolar) of the bcl-2/CRE hybrid oligomer is achieved about 1, 2, 3, 4, 5, 6, 7, 8, 9 or 10 hours after the administration of the bcl-2/CRE hybrid oligomer. In yet another embodiment, the circulating plasma concentration of at least 30 nM of the bcl-2/CRE hybrid oligomer is achieved in about 36 to 48 hours, preferably 24 to 35 hours, more preferably in 12 to 24 hours; most preferably in under 12 hours.

In a specific embodiment, the dose of a bcl-2/CRE hybrid oligomer is a high dose. In one embodiment, the circulating plasma concentration of the bcl-2/CRE hybrid oligomer is at least 30 nM. In another embodiment, the circulating level of bcl-2/CRE hybrid oligomer is 1 µM to 10 µM. In yet another embodiment, the circulating level of bcl-2/CRE hybrid oligomer is 1, 2, 3, 4, 5, 6, 7, 8, 9 or 10 µM. In yet another embodiment, the circulating level of bcl-2/CRE hybrid oligomer of 1 µM to 10 µM is achieved in about 36 to 48 hours, preferably 24 to 35 hours, more preferably in 12 to 24 hours; most preferably in under 12 hours.

The high dose may be achieved by several administrations per cycle. Alternatively, the high dose may be administered in a single bolus administration. A single administration of a high dose may result in circulating plasma levels of bcl-2/CRE hybrid oligomer that are transiently much higher than 30 nM. Moreover, single administrations of particularly high doses of a bcl-2/CRE hybrid oligomer may result in a circulating plasma concentration of bcl-2/CRE hybrid oligomer of 1 µM to 10 µM in much less 12 hours, even in less than one hour.

Additionally, the dose of a bcl-2/CRE hybrid oligomer may vary according to the particular bcl-2/CRE hybrid oligomer used. The dose employed is likely to reflect a balancing of considerations, among which are stability, localization, cellular uptake, and toxicity of the particular bcl-2/CRE hybrid oligomer. For example, a particular chemically modified bcl-2/CRE hybrid oligomer may exhibit greater resistance to degradation, or may exhibit higher affinity for the target nucleic acid, or may exhibit increased uptake by the cell or cell nucleus; all of which may permit the use of low doses. In yet another example, a particular chemically modified bcl-2/CRE hybrid oligomer may exhibit lower toxicity than other oligomers, and therefore can be used at high doses. Thus, for a given bcl-2/CRE hybrid oligomer, an appropriate dose to administer can be relatively high or relatively low. Appropriate doses would be appreciated by the skilled artisan, and the invention contemplates the continued assessment of optimal treatment schedules for particular species of bcl-2/CRE hybrid oligomers. The daily dose can be administered in one or more treatments.

Other factors to be considered in determining an effective dose of a bcl-2/CRE hybrid oligomer include whether the oligomer will be administered in combination with other therapeutics. In such cases, the relative toxicity of the other therapeutics may indicate the use of a bcl-2/CRE hybrid oligomer at low doses. Alternatively, treatment with a high dose of bcl-2/CRE hybrid oligomer can result in combination therapies with reduced doses of therapeutics. In a specific embodiment, treatment with a particularly high dose of bcl-2/CRE hybrid oligomer can result in combination therapies with greatly reduced doses of cancer therapeutics. For example, treatment of a patient with 10, 20, 30, 40, or 50 mg/kg/day of a bcl-2/CRE hybrid oligomer can further increase the sensitivity of a subject to additional cancer therapeutics. In such cases, the particularly high dose of bcl-2/CRE hybrid oligomer is combined with, for example, a greatly shortened radiation therapy schedule. In another example, the particularly high dose of a bcl-2/CRE hybrid oligomer produces significant enhancement of the potency of additional cancer therapeutic agents.

Additionally, the particularly high doses of bcl-2/CRE hybrid oligomer may further shorten the period of administration of a therapeutically effective amount of bcl-2 antisense oligomer, CRE decoy and/or cancer therapeutic, such that the length of a treatment cycle is much shorter than 14 days.

In a specific embodiment, the phosphorothioate hybrid oligomer of the sequence 5'-TGACGTCATCTC-CCAGCGTGCGCCATTGACGTCA-3' (SEQ ID NO:33) is administered for a short treatment cycle, defined as a period of less than two weeks.

In one embodiment, a bcl-2/CRE hybrid oligomer is administered for 2 to 13 days at a dose of 0.01 to 10 mg/kg/day. In a specific embodiment, a bcl-2/CRE hybrid oligomer is administered for 2 to 3, 4 to 5, 6 to 7, 8 to 9, 10 to 11, or 12 to 13 days at a dose of 0.01 to 1, 1 to 2, 3 to 4, 5 to 6, 6 to 7, 7 to 8, or 9 to 10 mg/kg/day; more preferably at a dose of 4 to 9 mg/kg/day, and most preferably at a dose of 5 to 7 mg/kg/day. In another embodiment, bcl-2/CRE hybrid oligomer is administered at said dose for 3 to 9 days. In yet another embodiment, bcl-2/CRE hybrid oligomer is administered at said dose for 4 to 7 days. In a preferred embodiment, bcl-2/CRE hybrid oligomer is administered at said dose for 5 to 6 days. In a most preferred embodiment, bcl-2/CRE hybrid oligomer is administered at a dose of 5 to 7 mg/kg/day for 5 to 6 days. The invention contemplates other preferred treatment regimens depending on the particular bcl-2/CRE hybrid oligomer to be used, or depending on the particular mode of administration, or depending on whether the bcl-2/CRE hybrid oligomer is administered as part of a combination therapy, e.g., in combination with other cancer therapeutic agents. The daily dose can be administered in one or more treatments.

In another embodiment, bcl-2/CRE hybrid oligomer is administered at a particularly high dose of about 10 to 50 mg/kg/day. In a specific embodiment, bcl-2/CRE hybrid oligomer is administered at a particularly high dose of about 10 to 15, 16 to 20, 21 to 25, 26 to 30, 31 to 35, 36 to 40, 41 to 45, or 46 to 50 mg/kg/day. In a further embodiment, bcl-2/CRE hybrid oligomer is administered at said dose for 1 to 10 days. In yet another embodiment, bcl-2/CRE hybrid oligomer is administered at said dose for 2 to 7 days. In a yet another embodiment, bcl-2/CRE hybrid oligomer is administered at said dose for 3 to 4 days. In a preferred embodiment, bcl-2/CRE hybrid oligomer is administered at a dose of 26 to 30, 31 to 35, 36 to 40, 41 to 45, or 46 to 50 mg/kg/day for a minimum of one day. The invention contemplates other preferred treatment regimens depending on the particular bcl-2/CRE hybrid oligomer to be used, or depending on the particular mode of administration, or depending on whether the bcl-2/CRE hybrid oligomer is administered as part of a combination therapy, e.g., in combination with a cancer therapeutic agent. The daily dose can be administered in one or more treatments.

In one embodiment, the invention provides a method for the use of a bcl-2/CRE hybrid oligomer, which is administered for the prevention or treatment of colon cancer.

In another embodiment, the invention provides a method for the use of a bcl-2/CRE hybrid oligomer, which is administered for the prevention and treatment of hepatitis B virus infection.

In another embodiment, the invention provides a method for the use of a bcl-2/CRE hybrid oligomer to inhibit the growth of cancer cells in vitro comprising contacting the cancer cells with a hybrid oligomer comprising a CRE sequence and a sequence that hybridizes to the bcl-2 pre-mRNA or mRNA.

4.6 Cancer Therapeutics

Normal, non-cancerous cells divide at a frequency characteristic for the particular cell type. When a cell has been transformed into a cancerous state, uncontrolled cell proliferation and reduced cell death results, and therefore, promiscuous cell division or cell growth is a hallmark of a cancerous cell type. Examples of types of cancer, include, but are not limited to, non-Hodgkin's lymphoma, Hodgkin's lymphoma, leukemia (e.g., acute leukemia such as acute lymphocytic leukemia, acute myelocytic leukemia, chronic myeloid leukemia, chronic lymphocytic leukemia, multiple myeloma), colon carcinoma, rectal carcinoma, pancreatic cancer, breast cancer, ovarian cancer, prostate cancer, renal cell carcinoma, hepatoma, bile duct carcinoma, choriocarcinoma, cervical cancer, testicular cancer, lung carcinoma, bladder carcinoma, melanoma, head and neck cancer, brain cancer, cancers of unknown primary site, neoplasms, cancers of the peripheral nervous system, cancers of the central nervous system, tumors (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, seminoma, embryonal carcinoma, Wilms' tumor, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, and retinoblastoma), heavy chain disease, metastases, or any disease or disorder characterized by uncontrolled or abnormal cell growth.

4.7 Methods of Use of Oligomers and Cancer Therapeutics

In a preferred embodiment, the invention further encompasses the use of combination therapy to prevent or treat cancer. For example, prostate cancer can be treated with a pharmaceutical composition comprising a CRE decoy oligomer, bcl-2 antisense oligomer and/or bcl-2/CRE hybrid oligomer in combination with paclitaxel, docetaxel, mitoxantrone, and/or an androgen receptor antagonist (e.g., flutamide). As another example, breast cancer can be treated with a pharmaceutical composition comprising a CRE decoy oligomer plus bcl-2 antisense oligomer and/or bcl-2/CRE hybrid oligomer in combination with docetaxel, paclitaxel, cisplatin, 5-fluorouracil, doxorubicin, and/or VP-16 (etoposide).

As another example, leukemia can be treated with a pharmaceutical composition comprising a CRE decoy oligomer plus bcl-2 antisense oligomer and/or bcl-2/CRE hybrid oligomer in combination with fludarabine, cytosine arabinoside, gemtuzumab (MYLOTARG), daunorubicin, methotrexate, vincristine, 6-mercaptopurine, idarubicin, mitoxantrone, etoposide, asparaginase, prednisone and/or cyclophosphamide. As another example, myeloma can be treated with a pharmaceutical composition comprising a CRE decoy oligomer plus bcl-2 antisense oligomer and/or bcl-2/CRE hybrid oligomer in combination with dexamethasone.

As another example, melanoma can be treated with a pharmaceutical composition comprising a CRE decoy oligomer plus bcl-2 antisense oligomer and/or bcl-2/CRE hybrid oligomer in combination with dacarbazine. As another example, colorectal cancer can be treated with a pharmaceutical composition comprising a CRE decoy oligomer plus bcl-2 antisense oligomer and/or bcl-2/CRE hybrid oligomer in combination with irinotecan. As another example, lung cancer can be treated with a pharmaceutical composition comprising a CRE decoy oligomer plus bcl-2 antisense oligomer and/or bcl-2/CRE hybrid oligomer in combination with paclitaxel, docetaxel, etoposide and/or cisplatin.

As another example, non-Hodgkin's lymphoma can be treated with a pharmaceutical composition comprising a CRE decoy oligomer plus bcl-2 antisense oligomer and/or bcl-2/CRE hybrid oligomer in combination with cyclophosphamide, CHOP, etoposide, bleomycin, mitoxantrone and/or cisplatin. As another example, gastric cancer can be treated with a pharmaceutical composition comprising a CRE decoy oligomer plus bcl-2 antisense oligomer and/or bcl-2/CRE hybrid oligomer in combination with cisplatin. As another example, pancreatic cancer can be treated with a pharmaceutical composition comprising a CRE decoy oligomer plus bcl-2 antisense oligomer and/or bcl-2/CRE hybrid oligomer in combination with gemcitabine. These combination therapies can also be used to prevent cancer or the recurrence of cancer.

Combination therapy also includes, in addition to administration of a CRE decoy oligomer plus bcl-2 antisense oligomer and/or bcl-2/CRE hybrid oligomer, the use of one or more molecules, compounds or treatments that aid in the prevention or treatment of cancer, which molecules, compounds or treatments includes, but is not limited to, chemoagents, immunotherapeutics, cancer vaccines, anti-angiogenic agents, cytokines, hormone therapies, gene therapies, and radiotherapies.

In one embodiment, one or more chemoagents, in addition to a CRE decoy oligomer plus bcl-2 antisense oligomer and/or bcl-2/CRE hybrid oligomer, is administered to treat a cancer patient. Examples of chemoagents contemplated by the present invention include, but are not limited to, cytosine arabinoside, taxoids (e.g., paclitaxel, docetaxel), anti-tubulin agents (e.g., paclitaxel, docetaxel, Epothilone B, or its analogues), cisplatin, carboplatin, adriamycin, tenoposide, mitozantron, 2-chlorodeoxyadenosine, alkylating agents (e.g., cyclophosphamide, mechlorethamine, thioepa, chlorambucil, melphalan, carmustine (BSNU), lomustine (CCNU), cyclothosphamide, busulfan, dibromomannitol, streptozotocin, mitomycin C, and cis-dichlorodiamine platinum (II) (DDP) cisplatin, thio-tepa), antibiotics (e.g., dactinomycin (formerly actinomycin), bleomycin, mithramycin, anthramycin), antimetabolites (e.g., methotrexate, 6-mercaptopurine, 6-thioguanine, cytarabine, 5-fluorouracil, fludarabine, gemcitabine, dacarbazine, temozolamide), asparaginase, *Bacillus Calmette* and *Guerin*, diphtheria toxin, hexamethylmelamine, hydroxyurea, LYSODREN®, nucleoside analogues, plant alkaloids (e.g., Taxol, paclitaxel, camptothecin, topotecan, irinotecan (CAMPTOSAR, CPT-11), vincristine, vinca alkyloids such as vinblastine), podophyllotoxin (including derivatives such as epipodophyllotoxin, VP-16 (etoposide), VM-26 (teniposide)), cytochalasin B, gramicidin D, ethidium bromide, emetine, mitomycin, procarbazine, mechlorethamine, anthracyclines (e.g., daunorubicin (formerly daunomycin), doxorubicin, doxorubicin liposomal), dihydroxyanthracindione, mitoxantrone, mithramycin, actinomycin D, procaine, tetracaine, lidocaine, propranolol, puromycin, anti-mitotic agents, abrin, ricin A, pseudomonas exotoxin, nerve growth factor, platelet derived growth factor, tissue plasminogen activator, aldesleukin, allutamine, anastrozle, bicalutamide, biaomycin, busulfan, capecitabine, carboplain, chlorabusil, cladribine, cylarabine, daclinomycin, estramusine, floxuridhe, gamcitabine, gosereine, idarubicin, itosfamide, lauprolide acetate, levamisole, lomusline, mechlorethamine, magestrol, acetate, mercaptopurino, mesna, mitolanc, pegaspergase, pentoslatin, picamycin, riuxlmab, campath-1, straplozocin, thioguanine, tretinoin, vinorelbine, or any fragments, family members, or derivatives thereof, including pharmaceutically acceptable salts thereof. Compositions comprising one or more chemoagents (e.g., FLAG, CHOP) are also contemplated by the present invention. FLAG comprises fludarabine, cytosine arabinoside (Ara-C) and G-CSF. CHOP comprises cyclophosphamide, vincristine, doxorubicin, and prednisone.

In one embodiment, said chemoagent is dacarbazine at a dose ranging from 200 to 4000 mg/m$^2$/cycle. In a preferred embodiment, said dose ranges from 700 to 1000 mg/m$^2$/cycle. In another embodiment, said chemoagent is fludarabine at a dose ranging from 25 to 50 mg/m$^2$/cycle. In another embodiment, said chemoagent is cytosine arabinoside (Ara-C) at a dose ranging from 200 to 2000 mg/m$^2$/cycle. In another embodiment, said chemoagent is docetaxel at a dose ranging from 1.5 to 7.5 mg/kg/cycle. In another embodiment, said chemoagent is paclitaxel at a dose ranging from 5 to 15 mg/kg/cycle. In yet another embodiment, said chemoagent is cisplatin at a dose ranging from 5 to 20 mg/kg/cycle. In yet another embodiment, said chemoagent is 5-fluorouracil at a dose ranging from 5 to 20 mg/kg/cycle. In yet another embodiment, said chemoagent is doxorubicin at a dose ranging from 2 to 8 mg/kg/cycle. In yet another embodiment, said chemoagent is epipodophyllotoxin at a dose ranging from 40 to 160 mg/kg/cycle. In yet another embodiment, said chemoagent is cyclophosphamide at a dose ranging from 50 to 200 mg/kg/cycle. In yet another embodiment, said chemoagent is irinotecan at a dose ranging from 50 to 75, 75 to 100, 100 to 125, or 125 to 150 mg/m$^2$/cycle. In yet another embodiment, said chemoagent is vinblastine at a dose ranging from 3.7 to 5.4, 5.5 to 7.4, 7.5 to 11, or 11 to 18.5 mg/m$^2$/cycle. In yet another embodiment, said chemoagent is vincristine at a dose ranging from 0.7 to 1.4, or 1.5 to 2 mg/m$^2$/cycle. In yet another embodiment, said chemoagent is methotrexate at a dose ranging from 3.3 to 5, 5 to 10, 10 to 100, or 100 to 1000 mg/m$^2$/cycle.

In a preferred embodiment, the invention further encompasses the use of low doses of chemoagents when administered as part of a CRE decoy oligomer plus bcl-2 antisense oligomer and/or bcl-2/CRE hybrid oligomer treatment regimen. For example, initial treatment with a CRE decoy oligomer plus bcl-2 antisense oligomer and/or bcl-2/CRE hybrid oligomer increases the sensitivity of a tumor to subsequent challenge with a dose of chemoagent, which dose is near or below the lower range of dosages when the chemoagent is administered without the oligomer. In one embodiment, a CRE decoy oligomer plus bcl-2 antisense oligomer and/or bcl-2/CRE hybrid oligomer and a low dose (e.g., 6 to 60 mg/m$^2$ day or less) of docetaxel are administered to a cancer patient. In another embodiment, a CRE decoy oligomer plus bcl-2 antisense oligomer and/or bcl-2/CRE hybrid oligomer and a low dose (e.g., 10 to 135 mg/m$^2$/day or less) of paclitaxel are administered to a cancer patient. In yet another embodiment, a CRE decoy oligomer plus bcl-2 antisense oligomer and/or bcl-2/CRE hybrid oligomer and a low dose (e.g., 2.5 to 25 mg/m$^2$/day or less) of fludarabine are administered to a cancer patient. In yet another embodiment, a CRE decoy oligomer plus bcl-2 antisense oligomer and/or bcl-2/CRE hybrid oligomer and a low dose (e.g., 0.5 to 1.5 g/m$^2$/day or less) of cytosine arabinoside (Ara-C) are administered to a cancer patient.

The invention, therefore, contemplates the use of a CRE decoy oligomer and one or more bcl-2 antisense oligomers or one or more bcl-2/CRE hybrid oligomers, which is administered prior to, subsequently, or concurrently with low doses of chemoagents, for the prevention or treatment of cancer.

In one embodiment, said chemoagent is cisplatin, e.g., PLATINOL or PLATINOL-AQ (Bristol Myers), at a dose ranging from 5 to 10, 10 to 20, 20 to 40, or 40 to 75 mg/m$^2$/cycle. In another embodiment, a dose of cisplatin ranging from 7.5 to 75 mg/m$^2$/cycle is administered to a patient with ovarian cancer. In another embodiment, a dose of cisplatin ranging from 5 to 50 mg/m$^2$/cycle is administered to a patient with bladder cancer.

In another embodiment, said chemoagent is carboplatin, e.g., PARAPLATIN (Bristol Myers), at a dose ranging from 2 to 4, 4 to 8, 8 to 16, 16 to 35, or 35 to 75 mg/m$^2$/cycle. In another embodiment, a dose of carboplatin ranging from 7.5 to 75 mg/m$^2$/cycle is administered to a patient with ovarian cancer. In another embodiment, a dose of carboplatin ranging from 5 to 50 mg/m$^2$/cycle is administered to a patient with bladder cancer. In another embodiment, a dose of carboplatin ranging from 2 to 20 mg/m$^2$/cycle is administered to a patient with testicular cancer.

In another embodiment, said chemoagent is cyclophosphamide, e.g., CYTOXAN (Bristol Myers Squibb), at a dose ranging from 0.25 to 0.5, 0.5 to 1, 1 to 2, 2 to 5, 5 to 10, 10 to 20, 20 to 40 mg/kg/cycle. In another embodiment, a dose of cyclophosphamide ranging from 4 to 40 mg/kg/cycle is administered to a patient with malignant cancer. In another embodiment, a dose of cyclophosphamide ranging from 0.25 to 2.5 mg/kg/cycle is administered to a patient with non-malignant cancer.

In one embodiment, said chemoagent is cytarabine, e.g., CYTOSAR-U (Pharmacia & Upjohn), at a dose ranging from 0.5 to 1, 1 to 4, 4 to 10, 10 to 25, 25 to 50, or 50 to 100 mg/m$^2$/cycle. In another embodiment, a dose of cytarabine ranging from 10 to 100 mg/m$^2$/cycle is administered to a patient with acute leukemia. In another embodiment, a dose of cytarabine ranging from 0.5 to 5 mg/m$^2$/cycle is administered to a patient with meningeal leukemia. In another embodiment, a dose of cytarabine liposome, e.g., DEPO-CYT (Chiron Corp.) ranging from 5 to 50 mg/m$^2$/cycle is administered to a patient with cancer.

In another embodiment, said chemoagent is dacarbazine, e.g., DTIC or DTIC-DOME (Bayer Corp.), at a dose ranging from 15 to 250 mg/m$^2$/cycle or ranging from 0.2 to 2 mg/kg/cycle. In another embodiment, a dose of dacarbazine ranging from 15 to 150 mg/m$^2$/cycle is administered to a patient with Hodgkin's disease. In another embodiment, a dose of dacarbazine ranging from 0.2 to 2 mg/kg/cycle is administered to a patient with malignant melanoma.

In another embodiment, said chemoagent is topotecan, e.g., HYCAMTIN (SmithKline Beecham), at a dose ranging from 0.1 to 0.2, 0.2 to 0.4, 0.4 to 0.8, or 0.8 to 1.5 mg/m$^2$/cycle.

In another embodiment, said chemoagent is irinotecan, e.g., CAMPTOSAR (Pharmacia & Upjohn), at a dose ranging from 5 to 10, 10 to 25, or 25 to 50 mg/m$^2$/cycle.

In another embodiment, said chemoagent is fludarabine, e.g., FLUDARA (Berlex Laboratories), at a dose ranging from 2.5 to 5, 5 to 10, 10 to 15, or 15 to 25 mg/m$^2$/cycle.

In another embodiment, said chemoagent is cytosine arabinoside (Ara-C) at a dose ranging from 200 to 2000 mg/m$^2$/cycle.

In another embodiment, said chemoagent is docetaxel, e.g., TAXOTERE (Rhone Poulenc Rorer) at a dose ranging from 6 to 10, 10 to 30, or 30 to 60 mg/m$^2$/cycle.

In another embodiment, said chemoagent is paclitaxel, e.g., TAXOL (Bristol Myers Squibb), at a dose ranging from 10 to 20, 20 to 40, 40 to 70, or 70 to 135 mg/kg/cycle.

In another embodiment, said chemoagent is 5-fluorouracil at a dose ranging from 0.5 to 5 mg/kg/cycle.

In another embodiment, said chemoagent is doxorubicin, e.g., ADRIAMYCIN (Pharmacia & Upjohn), DOXIL (Alza), RUBEX (Bristol Myers Squibb), at a dose ranging from 2 to 4, 4 to 8, 8 to 15, 15 to 30, or 30 to 60 mg/kg/cycle.

In another embodiment, said chemoagent is etoposide, e.g., VEPESID (Pharmacia & Upjohn), at a dose ranging from 3.5 to 7, 7 to 15, 15 to 25, or 25 to 50 mg/m$^2$/cycle. In another embodiment, a dose of etoposide ranging from 5 to 50 mg/m$^2$/cycle is administered to a patient with testicular cancer. In another embodiment, a dose of etoposide ranging from 3.5 to 35 mg/m$^2$/cycle is administered to a patient with small cell lung cancer.

In another embodiment, said chemoagent is vinblastine, e.g., VELBAN (Eli Lilly), at a dose ranging from 0.3 to 0.5, 0.5 to 1, 1 to 2, 2 to 3, or 3 to 3.7 mg/m$^2$/cycle.

In another embodiment, said chemoagent is vincristine, e.g., ONCOVIN (Eli Lilly), at a dose ranging from 0.1, 0.2, 0.3, 0.4, 0.5, 0.6 or 0.7 mg/m$^2$/cycle.

In another embodiment, said chemoagent is methotrexate at a dose ranging from 0.2 to 0.9, 1 to 5, 5 to 10, 10 to 20.

In another embodiment, a CRE decoy oligomer plus bcl-2 antisense oligomer and/or bcl-2/CRE hybrid oligomer is administered in combination with one or more immunotherapeutic agents, such as antibodies and immunomodulators, which includes, but is not limited to, rituxan, rituximab, campath-1, gemtuzumab, or trastuzumab.

In another embodiment, a CRE decoy oligomer plus bcl-2 antisense oligomer and/or bcl-2/CRE hybrid oligomer is administered in combination with one or more antiangiogenic agents, which includes, but is not limited to, angiostatin, thalidomide, kringle 5, endostatin, Serpin (Serine Protease Inhibitor) anti-thrombin, 29 kDa N-terminal and a 40 kDa C-terminal proteolytic fragments of fibronectin, 16 kDa proteolytic fragment of prolactin, 7.8 kDa proteolytic fragment of platelet factor-4, a 13-amino acid peptide corresponding to a fragment of platelet factor-4 (Maione et al., 1990, Cancer Res. 51:2077–2083), a 14-amino acid peptide corresponding to a fragment of collagen I (Tolma et al., 1993, J. Cell Biol. 122:497–511), a 19 amino acid peptide corresponding to a fragment of Thrombospondin I (Tolsma et al., 1993, J. Cell Biol. 122:497–511), a 20-amino acid peptide corresponding to a fragment of SPARC (Sage et al., 1995, J. Cell. Biochem. 57:1329–1334), or any fragments, family members, or derivatives thereof, including pharmaceutically acceptable salts thereof.

Other peptides that inhibit angiogenesis and correspond to fragments of laminin, fibronectin, procollagen, and EGF have also been described (see the review by Cao, 1998, Prog. Mol. Subcell. Biol. 20:161–176). Monoclonal antibodies and cyclic pentapeptides, which block certain integrins that bind RGD proteins (i.e., possess the peptide motif Arg-Gly-Asp), have been demonstrated to have anti-vascularization activities (Brooks et al., 1994, Science 264:569–571; Hammes et al., 1996, Nature Medicine 2:529–533). Moreover, inhibition of the urokinase plasminogen activator receptor by receptor antagonists inhibits angiogenesis, tumor growth and metastasis (Min et al., 1996, Cancer Res. 56: 2428–33; Crowley et al., 1993, Proc. Natl. Acad. Sci. USA 90:5021–25). Use of such antiangiogenic agents is also contemplated by the present invention.

In another embodiment, a CRE decoy oligomer plus bcl-2 antisense oligomer and/or bcl-2/CRE hybrid oligomer is administered in combination with a regimen of radiation.

In another embodiment, a bcl-2/CRE hybrid oligomer or CRE decoy oligomer plus bcl-2 antisense oligomer is administered in combination with one or more cytokines, which includes, but is not limited to, interferons, lymphokines, tumor necrosis factors, tumor necrosis factor-like cytokines, lymphotoxin-α, lymphotoxin-β, interferon-α, interferon-β, macrophage inflammatory proteins, granulocyte monocyte colony stimulating factor, interleukins (including, but not limited to, interleukin-1, interleukin-2, interleukin-6, interleukin-12, interleukin-15, interleukin-18), OX40, CD27, CD30, CD40 or CD137 ligands, Fas-Fas ligand, 4-1BBL, endothelial monocyte activating protein or any fragments, family members, or derivatives thereof, including pharmaceutically acceptable salts thereof.

In another embodiment, a bcl-2/CRE hybrid oligomer or CRE decoy oligomer plus bcl-2 antisense oligomer is administered in combination with one or more growth factors.

In yet another embodiment, a bcl-2/CRE hybrid oligomer or CRE decoy oligomer plus bcl-2 antisense oligomer is administered in combination with a cancer vaccine. Examples of cancer vaccines include, but are not limited to, autologous cells or tissues, non-autologous cells or tissues, carcinoembryonic antigen, alpha-fetoprotein, human chorionic gonadotropin, BCG live vaccine, melanocyte lineage proteins (e.g., gp100, MART-1/MelanA, TRP-1 (gp75), tyrosinase, widely shared tumor-specific antigens (e.g., BAGE, GAGE-1, GAGE-2, MAGE-1, MAGE-3, N-acetylglucosaminyltransferase-V, p15), mutated antigens that are tumor-specific (β-catenin, MUM-1, CDK4), nonmelanoma antigens (e.g., HER-2/neu (breast and ovarian carcinoma), human papillomavirus-E6, E7 (cervical carcinoma), MUC-1 (breast, ovarian and pancreatic carcinoma)). For human tumor antigens recognized by T cells, see generally Robbins and Kawakami, 1996, Curr. Opin. Immunol. 8:628–36. Cancer vaccines may or may not be purified preparations.

In yet another embodiment, a bcl-2/CRE hybrid oligomer or CRE decoy oligomer plus bcl-2 antisense oligomer is used in association with a hormonal treatment. Hormonal therapeutic treatments comprise hormonal agonists, hormonal antagonists (e.g., flutamide, tamoxifen, leuprolide acetate (LUPRON)), and steroids (e.g., dexamethasone, retinoids, betamethasone, cortisol, cortisone, prednisone, dehydrotestosterone, glucocorticoids, mineralocorticoids, estrogen, testosterone, progestins).

In yet another embodiment, a bcl-2/CRE hybrid oligomer or CRE decoy oligomer plus bcl-2 antisense oligomer is used in association with a gene therapy program in the treatment of cancer.

In one embodiment, a bcl-2/CRE hybrid oligomer or CRE decoy oligomer plus bcl-2 antisense oligomer is administered, in combination with at least one cancer therapeutic agent, for a short treatment cycle to a cancer patient to treat cancer. In one embodiment, said treatment cycle ranges from 2 to 13 days. In another embodiment, said treatment cycle ranges from 3 to 9 days. In another embodiment, said treatment cycle ranges from 4 to 7 days. In yet another embodiment, said treatment cycle ranges from 5 to 6 days. The duration of treatment with the cancer therapeutic agent may vary according to the particular cancer therapeutic agent used. The invention also contemplates discontinuous administration or daily doses divided into several partial administrations. An appropriate treatment time for a particular cancer therapeutic agent will be appreciated by the skilled artisan, and the invention contemplates the continued assessment of optimal treatment schedules for each cancer therapeutic agent.

The present invention contemplates at least one cycle, preferably more than one cycle during which a single therapeutic or sequence of therapeutics is administered. In a preferred embodiment, the cycle is shorter than 14 days. In one embodiment, the length of one cycle is 10–13 days. In a preferred embodiment, the length of one cycle is 7–9 days. In a most preferred embodiment, the length of one cycle is 5–6 days. An appropriate period of time for one cycle will be appreciated by the skilled artisan, as will the total number of cycles, and the interval between cycles. The invention contemplates the continued assessment of optimal treatment schedules for each bcl-2 antisense oligomer and cancer therapeutic agent.

4.8 Pharmaceutical Compositions

The present invention further provides for a pharmaceutical composition that comprises a bcl-2/CRE hybrid oligomer, CRE decoy oligomer and/or bcl-2 antisense oligomer; and a pharmaceutically acceptable carrier. Suitable pharmaceutically acceptable carriers include essentially chemically inert and nontoxic pharmaceutical compositions that do not interfere with the effectiveness of the biological activity of the pharmaceutical composition. Examples of suitable pharmaceutical carriers include, but are not limited to, saline solutions, glycerol solutions, ethanol, N-(1(2,3-dioleyloxy)propyl)-N,N,N-trimethylammonium chloride (DOTMA), diolesylphosphotidylethanolamine (DOPE), and liposomes. Such pharmaceutical compositions should contain a therapeutically effective amount of the compound, together with a suitable amount of carrier so as to provide the form for proper administration to the patient. The formulation should suit the mode of administration. For example, oral administration requires enteric coatings to protect the oligomer(s) from degradation within the gastrointestinal tract. In another example, the oligomer(s) may be administered in a liposomal formulation to shield the antisense oligomer from degradative enzymes, facilitate transport in circulatory system, and effect delivery across cell membranes to intracellular sites.

In another embodiment, a pharmaceutical composition comprises a bcl-2/CRE hybrid oligomer, CRE decoy oligomer, bcl-2 antisense oligomer, and/or one or more therapeutic agents; and a pharmaceutically acceptable carrier. In a particular embodiment, the pharmaceutical composition comprises a bcl-2/CRE hybrid oligomer or CRE decoy oligomer plus bcl-2 antisense oligomer and one or more cancer therapeutic agents; and a pharmaceutically acceptable carrier.

In one embodiment, a pharmaceutical composition, comprising a bcl-2/CRE hybrid oligomer, CRE decoy oligomer and/or bcl-2 antisense oligomer, with or without other therapeutic agents; and a pharmaceutically acceptable carrier, is at an effective dose.

In one embodiment, the pharmaceutical composition comprises a bcl-2/CRE hybrid oligomer, CRE decoy oligomer and/or bcl-2 antisense oligomer at a dose of about 0.01 to 0.1, 0.1 to 1, 1 to 5, or 6 to 10 mg/kg/day; preferably at a dose of 4 to 9 mg/kg/day; more preferably at a dose of 5 to 7 mg/kg/day; and a pharmaceutically acceptable carrier. In another embodiment, the pharmaceutical composition comprises a bcl-2/CRE hybrid oligomer, CRE decoy oligomer and/or bcl-2 antisense oligomer at a dose of 0.01, 0.025, 0.05, 0.075, 1, 2, 3, 4, 5, 6, 7, 8, 9 or 10 mg/kg/day; and a pharmaceutically acceptable carrier. The actual amount of any particular antisense oligomer administered can depend on several factors, such as the type of cancer, the toxicity of the antisense oligomer to normal cells of the body, the rate of uptake of the antisense oligomer by tumor cells, and the weight and age of the individual to whom the antisense oligomer is administered. Because of the many factors present in vivo that may interfere with the action or biological activity of the antisense oligomer, an effective amount of the antisense oligomer may vary for each individual.

In another embodiment, the pharmaceutical compositions of the invention comprise a particularly high dose, which ranges from about 10 to 50 mg/kg/day. In a specific embodiment, a particularly high dose of bcl-2/CRE hybrid oligomer, CRE decoy oligomer and/or bcl-2 antisense oligomer, ranging from 11 to 20, 21 to 30, 31 to 40, or 41 to 50 mg/kg/day, is administered during a treatment cycle. In another specific embodiment, the particularly high dose of bcl-2/CRE hybrid oligomer, CRE decoy oligomer and/or bcl-2 antisense oligomer, ranges from 11 to 15, 16 to 20, 21 to 25, 26 to 30, 31 to 35, 36 to 40, 41 to 45, or 46 to 50 mg/kg/day during a treatment cycle.

Selection of the preferred effective dose can be determined (e.g., via clinical trials) by a skilled artisan based upon the consideration of several factors which will be known to one of ordinary skill in the art. Such factors include the particular form of antisense oligomer, the oligomer's pharmacokinetic parameters such as bioavailability, metabolism, half-life, etc., which is established during the development procedures typically employed in obtaining regulatory approval of a pharmaceutical compound. Further factors in considering the dose include the disease to be treated, the benefit to be achieved in a patient, the patient's body mass, the patient's immune status, the route of administration, whether administration of the antisense oligomer or combination therapeutic agent is acute or chronic, concomitant medications, and other factors known by the skilled artisan to affect the efficacy of administered pharmaceutical agents.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In a preferred embodiment, the composition is formulated in accordance with routine procedures as a pharmaceutical composition adapted for subcutaneous injection or intravenous administration to humans. Typically, pharmaceutical compositions for subcutaneous injection or intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where the composition is to be administered by infusion, it can be dispensed with an infusion bottle, bag, or other acceptable container, containing sterile pharmaceutical grade water, saline, or other acceptable diluents. Where the composition is administered by injection, an ampule of sterile water for injection or saline can be provided so that the ingredients may be mixed prior to administration.

4.9 Modes of Administration

Administration of the pharmaceutical compositions of the invention includes, but is not limited to, oral, intravenous infusion, subcutaneous injection, intramuscular, topical, depo injection, implantation, time-release mode, intracavitary, intranasal, inhalation, intratumor, intraocular, and controlled release. The pharmaceutical compositions of the invention also may be introduced parenterally, transmucosally (e.g., orally), nasally, rectally, intravaginally, sublingually, submucosally, or transdermally. Preferably, administration is parenteral, i.e., not through the alimentary canal but rather through some other route via, for example, intravenous, subcutaneous, intramuscular, intraperitoneal, intraorbital, intracapsular, intraspinal, intrastemal, intra-arterial, or intradermal administration. The skilled artisan can appreciate the specific advantages and disadvantages to be considered in choosing a mode of administration. Multiple modes of administration are encompassed by the invention. For example, a bcl-2/CRE hybrid oligomer, bcl-2 antisense oligomer, and/or CRE decoy oligomer is administered by subcutaneous injection, whereas a combination therapeutic agent is administered by intravenous infusion. Moreover, administration of one or more species of bcl-2 antisense oligomer, with or without other therapeutic agents, may occur simultaneously (i.e., co-administration) or sequentially. For example, a bcl-2/CRE hybrid oligomer, bcl-2 antisense oligomer, and/or CRE decoy oligomer is first administered to increase sensitivity of a tumor to subsequent administration of a cancer therapeutic agent or irradiation therapy. In another embodiment, the periods of administration of one or more species of bcl-2/CRE hybrid oligomer, CRE decoy oligomer, and/or bcl-2 antisense oligomer, with or without other therapeutic agents may overlap. For example, a bcl-2 antisense oligomer and CRE decoy oligomer is administered for 7 days, and a second therapeutic agent is introduced beginning on the fifth day of bcl-2 antisense and CRE decoy oligomer treatment, and treatment with the second therapeutic agent continues beyond the 7-day bcl-2 antisense and CRE decoy oligomer treatment.

Pharmaceutical compositions adapted for oral administration may be provided, for example, as capsules or tablets; as powders or granules; as solutions, syrups or suspensions (in aqueous or non-aqueous liquids); as edible foams or whips; or as emulsions. Tablets or hard gelatine capsules may comprise, for example, lactose, starch or derivatives thereof, magnesium stearate, sodium saccharine, cellulose, magnesium carbonate, stearic acid or salts thereof. Soft gelatine capsules may comprise, for example, vegetable oils, waxes, fats, semi-solid, or liquid polyols etc. Solutions and syrups may comprise, for example, water, polyols and sugars.

An active agent intended for oral administration may be coated with or admixed with a material (e.g., glyceryl monostearate or glyceryl distearate) that delays disintegration or affects absorption of the active agent in the gastrointestinal tract. Thus, for example, the sustained release of an active agent may be achieved over many hours and, if necessary, the active agent can be protected from being degraded within the gastrointestinal tract. Taking advantage of the various pH and enzymatic conditions along the gastrointestinal tract, pharmaceutical compositions for oral administration may be formulated to facilitate release of an active agent at a particular gastrointestinal location.

Pharmaceutical compositions adapted for parenteral administration include, but are not limited to, aqueous and non-aqueous sterile injectable solutions or suspensions, which may contain antioxidants, buffers, bacteriostats and solutes that render the pharmaceutical compositions substantially isotonic with the blood of an intended recipient. Other components that may be present in such pharmaceutical compositions include water, alcohols, polyols, glycerine and vegetable oils, for example. Compositions adapted for parenteral administration may be presented in unit-dose or multi-dose containers, for example sealed ampules and vials, and may be stored in a freeze-dried (lyophilized) condition requiring the addition of a sterile liquid carrier, e.g., sterile saline solution for injections, immediately prior to use. Extemporaneous injection solutions and suspensions may be prepared from sterile powders, granules and tablets. Such pharmaceutical compositions should contain a therapeutically effective amount of a bcl-2/CRE hybrid oligomer or CRE decoy oligomer plus bcl-2 antisense oligomer or other therapeutic agent, together with a suitable amount of carrier so as to provide the form for proper administration to the patient. The formulation should suit the mode of administration.

Pharmaceutical compositions adapted for transdermal administration may be provided as discrete patches intended to remain in intimate contact with the epidermis for a prolonged period of time. Pharmaceutical compositions adapted for topical administration may be provided as, for example, ointments, creams, suspensions, lotions, powders, solutions, pastes, gels, sprays, aerosols or oils. A topical ointment or cream is preferably used for topical administration to the skin, mouth, eye or other external tissues. When formulated in an ointment, the active ingredient may be employed with either a paraffinic or a water-miscible ointment base. Alternatively, the active ingredient may be formulated in a cream with an oil-in-water base or a water-in-oil base.

Pharmaceutical compositions adapted for topical administration to the eye include, for example, eye drops or injectable pharmaceutical compositions. In these pharmaceutical compositions, the active ingredient can be dissolved or suspended in a suitable carrier, which includes, for example, an aqueous solvent with or without carboxymethylcellulose. Pharmaceutical compositions adapted for topical administration in the mouth include, for example, lozenges, pastilles and mouthwashes.

Pharmaceutical compositions adapted for nasal administration may comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, pharmaceutical compositions adopted for nasal administration may comprise liquid carriers such as, for example, nasal sprays or nasal drops. These pharmaceutical compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient.

Pharmaceutical compositions adapted for rectal administration may be provided as suppositories or enemas. Pharmaceutical compositions adapted for vaginal administration may be provided, for example, as pessaries, tampons, creams, gels, pastes, foams or spray formulations.

In one embodiment, a pharmaceutical composition of the invention is delivered by a controlled-release system. For example, the pharmaceutical composition may be administered using intravenous infusion, an implantable osmotic pump, a transdermal patch, liposomes, or other modes of administration. In one embodiment, a pump may be used (See, e.g., Langer, 1990, Science 249:1527–33; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, the compound can be delivered in a vesicle, in particular a liposome (See, e.g., Langer, Science 249:1527–33 (1990); Treat et al., 1989, in *Liposomes in the Therapy of Infectious Disease and Cancer*, Lopez-Berestein and Fidler (eds.), Liss, New York, pp. 353–65; Lopez-Berestein, ibid., pp. 317–27 International Patent Publication No. WO 91/04014; U.S. Pat. No. 4,704, 355). In another embodiment, polymeric materials can be used (See, e.g., *Medical Applications of Controlled Release*, Langer and Wise (eds.), CRC Press: Boca Raton, Fla., 1974; *Controlled Drug Bioavailability, Drug Product Design and Performance*, Smolen and Ball (eds.), Wiley: New York (1984); Ranger and Peppas, 1953, J. Macromol. Sci. Rev. Macromol. Chem. 23:61; Levy et al., 1985, Science 228: 190; During et al., 1989, Ann. Neurol. 25:351; Howard et al., 1989, J. Neurosurg. 71:105).

In yet another embodiment, a controlled release system can be placed in proximity of the target. For example, a micropump may deliver controlled doses directly into the brain, thereby requiring only a fraction of the systemic dose (See, e.g., Goodson, 1984, in *Medical Applications of Controlled Release*, vol. 2, pp. 115–138).

In one embodiment, it may be desirable to administer the pharmaceutical composition of the invention locally to the area in need of treatment; this may be achieved, for example, and not by way of limitation, by local infusion during surgery, topical application (e.g., in conjunction with a wound dressing after surgery), injection, by means of a catheter, by means of a suppository, or by means of an implant. An implant can be of a porous, non-porous, or gelatinous material, including membranes, such as sialastic membranes, or fibers.

Suppositories generally contain active ingredients in the range of 0.5% to 10% by weight. Oral formulations preferably contain 10% to 95% active ingredient by weight.

A bcl-2/CRE hybrid oligomer, CRE decoy oligomer, and/or bcl-2 antisense oligomer can be administered before, during, and/or after the administration of one or more therapeutic agents. In one embodiment, a bcl-2/CRE hybrid oligomer, CRE decoy oligomer, and/or bcl-2 antisense oligomer can first be administered to reduce the expression of bcl-2, which increases the tumor's sensitivity to subsequent challenge with a cancer therapeutic agent. In another embodiment, a bcl-2 antisense oligomer, CRE decoy oligomer and/or bcl-2/CRE hybrid oligomer can be administered after administration of a cancer therapeutic agent to reduce tumor expression of bcl-2, which can deter tumor resistance, and thereby prevent relapse or minimization of response to the cancer therapeutic agent. In yet another embodiment, there can be a period of overlap between the administration of bcl-2/CRE hybrid oligomer, CRE decoy oligomer, and/or bcl-2 antisense oligomer and/or one or more therapeutic agents.

The invention further provides a pharmaceutical kit comprising an effective amount of a bcl-2/CRE hybrid oligomer, CRE decoy oligomer and/or bcl-2 antisense oligomer, in combination with a cancer therapeutic agent, to protect from or treat a cell-proliferative related disorder. In one embodiment, an effective amount of a bcl-2/CRE hybrid oligomer, CRE decoy oligomer, and/or bcl-2 antisense oligomer, and a pharmaceutically acceptable carrier, are packaged in a single dose vial or other container. In a particular embodiment, an effective amount of one or more CRE decoy oligomers and one or more bcl-2 antisense oligomers and a pharmaceutically acceptable carrier, are packaged in a single dose vial or other container. In a specific embodiment, the bcl-2 oligomer comprises the sequence 5'-TCTCCCAGCGTGCGCCAT-3' (SEQ ID NO:17), and the CRE decoy oligomer comprises the sequence 5'-TGACGTCATGACGTCATGACGTCA-3' (SEQ ID NO:36). In another specific embodiment, the bcl-2 oligomer comprises the sequence 5'-TCTCCCAGCGTGCGCCAT-3' (SEQ ID NO:17), and the CRE decoy oligomer comprises the sequence 5'-TGACGTCATTTTTGACGTCA-3' (SEQ ID NO:37). In another specific embodiment, the bcl-2 oligomer comprises the sequence 5'-TCTCCCAGCGTGCGCCAT-3' (SEQ ID NO:17), and the CRE decoy oligomer comprises the sequence 5'-TGACGTCATTTTGACGTCA-3' (SEQ ID NO:38). In another specific embodiment, the bcl-2 oligomer comprises the sequence 5'-TCTCCCAGCGTGCGCCAT-3' (SEQ ID NO:17), and the CRE decoy oligomer comprises the sequence 5'-TGACGTCATTTGACGTCA-3' (SEQ ID NO:39). In yet another specific embodiment, the bcl-2 oligomer comprises the sequence 5'-TCTCCCAGCGTGCGCCAT-3' (SEQ ID NO:17), and the CRE decoy oligomer comprises the sequence 5'-TGACGTCATTGACGTCA-3' (SEQ ID NO:40). The kit may comprise one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention may be better understood by reference to the following non-limiting Examples, which are provided only as exemplary of the invention. The following examples are presented to more fully illustrate the preferred embodiments of the invention. They should in no way be construed, however, as limiting the broader scope of the invention.

5. EXAMPLE 1

Studies of the Melting Temperature of Bcl-2 Antisense, CRE, and bcl-2/CRE Hybrid Oligomers In order to assess the thermodynamic stability of potentially useful hybrid oligomers, the melting temperatures of several constructs were tested. This example compares the melting temperatures of several structured "stem loop" oligonucleotides, alone and in combination with a target RNA. In this study, the melting temperatures of six self-complementary all-phosphorothioate oligonucleotides are compared to all-phosphodiester oligonucleotides. The phosphorothioate oligonucleotides each have two CRE arms, which are complementary and, therefore, self-hybridize to form the stem of a hairpin loop.

Six of the oligomers presented in Table 1 are variants having sequences that differ in the hairpin loop, while maintaining an N-terminal and a C-terminal CRE consensus sequence of TGACGTCA. The loop region of one oligonucleotide is the bcl-2 antisense 18-mer. The loop of another oligonucleotides is another copy of the CRE sequence. The loops of the other oligonucleotides comprise either 4, 3, 2, or 1 thymidines as the loop region. In addition to these six oligonucleotides, the bcl-2/CRE antisense hybrid phosphorothioate is compared to the bcl-2/CRE phosphodiester in the presence of the bcl-2 RNA target region from −3 to +20.

The self-complementary all-phosphorothioate oligonucleotides generally showed lower melting temperatures relative to all-phosphodiester oligomers. The melting temperatures increased as the size of the non-complementary loop decreased in size. Also, stem-loop structures containing the G3139 sequence flanked by self-complementary arms gave significantly different melting temperatures against target bcl-2 RNA. Phosphorothioate CRE flanking G3139 produced a far more significant temperature shift than the all-phosphodiester oligomer when melted against target bcl-2 RNA.

A modified buffer system was chosen to yield conditions relevant to several cell-free reactions, as well as to more closely resemble intracellular conditions.

5.1 Materials and Methods

Oligonucleotide sequences and functional regions are shown in Table 1.

TABLE 1

BK1-PS (phosphorothioate DNA)
5' <u>tga cgt cat</u> ctc cca gcg tgc gcc at<u>t gac gtc a</u> 3'          34-mer (SEQ ID NO:33)
(complementary arms are underlined, bcl-2 complement is in bold)

BK2-PS (phosphorothioate DNA)
5' tga cgt cat gac gtc atg acg tca 3'                                    24-mer (SEQ ID NO:36)

BK3-PS (phosphorothioate DNA)
5' tga cgt cat ttt tga cgt ca 3'                                         20-mer (SEQ ID NO:37)

BK4-PS (phosphorothioate DNA)
5' tga cgt cat ttt gac gtc a 3'                                          19-mer (SEQ ID NO:38)

BK5-PS (phosphorothioate DNA)
5' tga cgt cat tt gac gtc a 3'                                           18-mer (SEQ ID NO:39)

TABLE 1-continued

```
BK6-PS (phosphorothioate DNA)
5' tga cgt cat tga cgt ca 3'                                            17-mer (SEQ ID NO:40)

BK7-DE (all-phosphodiester DNA)
5' tga cgt cat ctc cca gcg tgc gcc att gac gtc a 3'                     34-mer (SEQ ID NO:33)

1084 RNA Target (BCL2 RNA target region from -3 to +20)
5' agg ata gcg cac gct ggg aga ac 3'                                    (SEQ ID NO:42)
(G3139 complement is underlined)
```

Oligonucleotides were synthesized according to standard methods. Melting temperatures were determined by UV absorbance in sealed one-cm quartz cuvettes using a Varian Cary 3E UV-visible spectrophotometer with a Varian Cary temperature controller and Cary 01.01 (4) Thermal software. The temperature of the heating block inside the spectrophotometer was monitored by an internal thermocouple. All mixtures were heated to 80° C. for 10–15 minutes, and then allowed to cool to room temperature before use.

Oligonucleotide probes and DNA targets were at 0.35 to 4.0 O.D. each per milliliter in a physiologically and enzymatically relevant buffer system as follows:

100 mM NaCl
80 mM KCl
8 mM $MgCl_2$
2% w/v sucrose
16 mM Tris-HCl
1 mM $NaH_2PO_4$
0.02 mM EDTA
pH=7.0 at 20° C.

Multiple melting temperature determinations were performed for each probe/target combination. Temperature gradients were run from low to high temperatures and visa versa due to the time lag required for temperature equilibration within the cuvettes relative to the monitored heat block. On average, the two runs varied by 2 to 3 degrees, and the average temperature represents the accurate temperature inside the cuvette during the maximum O.D. deflection with a standard deviation of less than 1° C.

5.2 Results

TABLE 2

| Name | Oligonucleotide Sequence 5'-3' (Target RNA 3'-5', RNA/DNA duplex underlined) | $T_m$ ave. ramp up | $T_m$ ave. ramp down | $T_m$ ° C. Ave ± SD |
|---|---|---|---|---|
| BK1-PS | tga cgt cat ctc cca gcg tgc gcc att gac gtc a (SEQ ID NO:33) | 51.1 | 46.2 | 48.7 ± 0.9 |
| BK2-PS | tga cgt cat gac gtc atg acg tca (SEQ ID NO:36) | 60.8 | 58.4 | 59.6 |
| BK3-PS | tga cgt cat ttt tga cgt ca (SEQ ID NO:37) | 64.3 | 60.3 | 62.3 |
| BK4-PS | tga cgt cat ttt gac gtc a (SEQ ID NO:38) | 62.8 | 61.7 | 62.3 |
| BK5-PS | tga cgt cat ttg acg tca (SEQ ID NO:39) | 63.5 | 60.1 | 61.8 ± 1.3 |
| BK6-PS | tga cgt cat tga cgt ca (SEQ ID NO:40) | 61.6 | 62.4 | 62.0 |
| BK7-PS | tga cgt cat ctc cca gcg tgc gcc att gac gtc a (SEQ ID NO:33) | 63.4 | 60.4 | 61.9 ± 0.9 |
| BK1-PS + 1084 | tga cgt ca_t ctc cca gcg tgc gcc at_t gac gtc a (SEQ ID NO:33) caa gag ggt cgc acg cgg tag ga (SEQ ID NO:42) | 3.7 | 72.4 | 73.1 |
| BK7-DE + 1084 | tga cgt ca_t ctc cca gcg tgc gcc at_t gac gtc a (SEQ ID NO:33) caa gag ggt cgc acg cgg tag ga (SEQ ID NO:42) | 80.4 | 78.3 | 79.4 |

Six phosphorothioate oligonucleotides with self-complementary CRE arms flanking various loop regions were compared for melting temperatures (Table 2). The first loop was the 18-mer Bcl-2 antisense oligomer (BK1-PS). Another loop was the 8-mer CRE sequence (BK2-PS). The other loops were composed of 4 (BK3-PS), 3(BK4-PS), 2 (BK5-PS) or 1 (BK6-PS) thymidine residues. All of these were compared to an all-phosphodiester DNA oligonucleotide (BK7-DE) with the same sequence as BK1-PS. The phosphorothioate (-PS) oligonucleotides demonstrated decreased melting temperatures relative to BK7-DE. The all-phosphorothioate oligonucleotides, BK1-PS through BK6-PS, demonstrated increased melting temperatures as the length of the non-complementary loop decreased, such that the melting temperature leveled off at 62° C. (BK3-PS through BK6-PS).

True stem-loop structures containing the G3139 sequence flanked by self-complementary arms (BK1-PS and BK7-DE) were compared against target BCL2 RNA. The phosphorothioate and all-phosphodiester DNA oligomers gave significantly different melting temperatures against target bcl-2 RNA (73° C. vs. 79° C. respectively). Also, BK1-PS gave a far more significant temperature shift when melted against bcl-2 RNA (49° C. shifted to 73° C.) than did the all-phosphodiester DNA BK7-DE (62° C. vs. 79° C.).

5.3 Conclusion

As loop size decreased in the phosphorothioate oligomers, melting temperature increased. Although the shift in melting temperature for BK1-PS and BK7-DE was significantly different, the actual melting temperature did not differ by more than 6 degrees. Therefore, both BK1-PS and BK7-DE can act as molecular beacons to detect BCL2 RNA. Finally, the G3139 target sequence represented in the 1084 RNA fragment used in this study could be useful as a reagent to detect G3139 oligonucleotide.

All references cited herein are specifically incorporated by reference as if fully set forth herein.

Having hereinabove disclosed exemplary embodiments of the present invention, those skilled in the art will recognize that this disclosure is only exemplary such that various alternatives, adaptations, and modifications are within the scope of the invention, and are contemplated by the Applicants. Accordingly, the present invention is not limited to the specific embodiments as illustrated above, but is defined by the following claims.

I claim:

1. A hybrid oligonucleotide comprising a CRE sequence and a sequence that hybridizes to a bcl-2 pre-mRNA or mRNA.

2. The hybrid oligonucleotide of claim 1, wherein the sequence which hybridizes to the bcl-2 pre-mRNA or mRNA comprises at least 10 consecutive bases that are complementary to the bcl-2 pre-mRNA or mRNA.

3. The hybrid oligonucleotide of claim 1, wherein the sequence that hybridizes to the bcl-2 pre-mRNA or mRNA comprises 5'-TCTCCCAGCG-3' (SEQ ID NO:35).

4. The hybrid oligonucleotide of claim 1, wherein the CRE sequence comprises 5'-TGACGTCA-3'.

5. The hybrid oligonucleotide of claim 4, further comprising the sequence 5'-TCTCCCAGCG-3' (SEQ ID NO:35).

6. The hybrid oligonucleotide of claim 1, wherein the CRE sequence is linked to the sequence that hybridizes to the bcl-2 pre-mRNA or mRNA.

7. The hybrid oligonucleotide of claim 6, wherein the CRE sequence comprises two or more CRE consensus sequences.

8. The hybrid oligonucleotide of claim 7, wherein a first CRE consensus sequence is linked to a second CRE consensus sequence by one or more bases.

9. A method of inhibiting the growth of cancer cells in vitro comprising contacting the cancer cells with a hybrid oligonucleotide comprising a CRE sequence and a sequence that hybridizes to a bcl-2 pre-mRNA or mRNA.

10. The method of claim 9, wherein the sequence which hybridizes to the bcl-2 pre-mRNA or mRNA comprises at least 10 consecutive bases that are complementary to the bcl-2 pre-mRNA or mRNA.

11. The method of claim 9, wherein the sequence that hybridizes to the bcl-2 pre-mRNA or mRNA comprises 5'-TCTCCCAGCG-3' (SEQ ID NO:35).

12. The method of claim 9, wherein the CRE sequence comprises 5'-TGACGTCA-3'.

13. The method of claim 12, wherein the hybrid oligonucleotide further comprises the sequence 5'-TCTCCCAGCG-3' (SEQ ID NO:35).

14. The method of claim 9, wherein the CRE sequence is linked to the sequence that hybridizes to the bcl-2 pre-mRNA or mRNA.

15. The method of claim 14, wherein the CRE sequence comprises two or more CRE consensus sequences.

16. The method of claim 15, wherein a first CRE consensus sequence is linked to a second CRE consensus sequence by one or more bases.

17. The method of claim 9, further comprising contacting the cancer cells with a bcl-2 antisense oligonucleotide.

18. The method of claim 9, further comprising contacting the cancer cells with a CRE decoy oligonucleotide.

19. The method of claim 9, further comprising contacting the cancer cells with a bcl-2 antisense oligonucleotide and a CRE decoy oligonucleotide.

20. The method of claim 9, further comprising contacting the cancer cells with one or more cancer therapeutic agents.

21. A method of treating cancer in a human comprising administering to said human, in which such treatment is desired, a hybrid oligonucleotide comprising a CRE sequence and a sequence that hybridizes to the bcl-2 pre-mRNA or mRNA.

22. The method of claim 21, wherein the sequence, which hybridizes to the bcl-2 pre-mRNA or mRNA comprises at least 10 consecutive bases that are complementary to the bcl-2 pre-mRNA or mRNA.

23. The method of claim 21, wherein the sequence that hybridizes to the bcl-2 pre-mRNA or mRNA comprises 5'-TCTCCCAGCG-3' (SEQ ID NO:35).

24. The method of claim 21, wherein the CRE sequence comprises 5'-TGACGTCA-3'.

25. The method of claim 24, wherein the hybrid oligonucleotide further comprises the sequence 5'-TCTCCAGCG-3' (SEQ ID NO:35).

26. The method of claim 21, wherein the CRE sequence is linked to the sequence that hybridizes to the bcl-2 pre-mRNA or mRNA.

27. The method of claim 26, wherein the CRE sequence comprises two or more CRE consensus sequences.

28. The method of claim 27, wherein a first CRE consensus sequence is linked to a second CRE consensus sequence by one or more bases.

29. The method of claim 21, further comprising administering a bcl-2 antisense oligonucleotide.

30. The method of claim 21, further comprising administering a CRE decoy oligonucleotide.

31. The method of claim 21, further comprising administering a bcl-2 antisense oligonucleotide and a CRE decoy oligonucleotide.

32. The method of claim 31, further comprising administering one or more cancer therapeutic agents.

33. The method of claim 32, wherein administration of the cancer therapeutic agent follows administration of the bcl-2 antisense oligonucleotide and the CRE decoy oligonucleotide.

34. The method of claim 32, wherein administration of the cancer therapeutic agent precedes administration of the bcl-2 antisense oligonucleotide and the CRE decoy oligonucleotide.

35. The method of claim 32, wherein the cancer therapeutic agent is administered concurrently with the bcl-2 antisense oligonucleotide and the CRE decoy oligonucleotide.

36. The method of claim 32, wherein said cancer therapeutic agent is a chemoagent, radiotherapeutic, immunotherapeutic, cancer vaccine, anti-angiogenic agent, cytokine, gene therapeutic, or hormonal agent.

37. The method of claim 32, wherein said cancer therapeutic agent is a chemoagent, and wherein said chemoagent is dacarbazine, docetaxel, paclitaxel, cisplatin, 5-fluorouracil, doxorubicin, etoposide, cyclophosphamide, fludarabine, irinotecan, or cytosine arabinoside (Ara-C).

38. The method of claim 32, wherein said cancer therapeutic agent is administered at a reduced dose.

39. The method of claim 21, wherein said administration is by oral, intravenous infusion, subcutaneous injection, intramuscular injection, topical, depo injection, implantation, time-release mode, intracavitary, intranasal, inhalation, intratumor, or intraocular administration.

40. The method of claim 21, wherein the hybrid oligonucleotide is administered for a period consisting of 2 to 13 days.

41. The method of claim 21, wherein the hybrid oligonucleotide is administered for a period consisting of 14 to 28 days.

42. The method of claim 21, comprising administering 0.01 to 10 mg/kg/day of the hybrid oligonucleotide.

43. The method of claim 21, comprising administering 10 to 50mg/kg/day of the hybrid oligonucleotide.

44. A pharmaceutical composition comprising a hybrid oligonucleotide comprising a CRE sequence and a sequence that hybridizes to a bcl-2 pre-mRNA or mRNA; and a pharmaceutically acceptable carrier.

45. The pharmaceutical composition of claim 44 further comprising a bcl-2 antisense oligonucleotide.

46. The pharmaceutical composition of claim 44 further comprising a CRE decoy oligonucleotide.

47. The pharmaceutical composition of claim 44 further comprising a bcl-2 antisense oligonucleotide a CRE decoy oligonucleotide.

48. A pharmaceutical composition comprising a CRE decoy oligonucleotide and a bcl-2 antisense oligonucleotide; and a pharmaceutically acceptable carrier.

* * * * *

SEQUENCE LISTING

```
<160> NUMBER OF SEQ ID NOS: 43

<210> SEQ ID NO 1
<211> LENGTH: 20
<212> TYPE: DNA
<213> ORGANISM: Artificial sequence
<220> FEATURE:
<223> OTHER INFORMATION: Description of artificial sequence: Synthetic Antisense
      Oligonucleotide

<400> SEQUENCE: 1
cagcgtgcgc catccttccc                                              20

<210> SEQ ID NO 2
<211> LENGTH: 35
<212> TYPE: DNA
<213> ORGANISM: Artificial sequence
<220> FEATURE:
<223> OTHER INFORMATION: Description of artificial sequence: Synthetic Antisense
      Oligonucleotide

<400> SEQUENCE: 2
cttttcctct gggaaggatg gcgcacgctg ggaga                             35

<210> SEQ ID NO 3
<211> LENGTH: 20
<212> TYPE: DNA
<213> ORGANISM: Artificial sequence
<220> FEATURE:
<223> OTHER INFORMATION: Description of artificial sequence: Synthetic Antisense
      Oligonucleotide

<400> SEQUENCE: 3
gatgcaccta cccagcctcc                                              20

<210> SEQ ID NO 4
<211> LENGTH: 33
<212> TYPE: DNA
<213> ORGANISM: Artificial sequence
<220> FEATURE:
<223> OTHER INFORMATION: Description of artificial sequence: Synthetic Antisense
      Oligonucleotide

<400> SEQUENCE: 4
```

```
        acggggtacg gaggctgggt aggtgcatct ggt                             33

<210> SEQ ID NO 5
<211> LENGTH: 20
<212> TYPE: DNA
<213> ORGANISM: Artificial sequence
<220> FEATURE:
<223> OTHER INFORMATION: Description of artificial sequence: Synthetic Antisense
      Oligonucleotide

<400> SEQUENCE: 5
acaaaggcat cctgcagttg                                            20

<210> SEQ ID NO 6
<211> LENGTH: 36
<212> TYPE: DNA
<213> ORGANISM: Artificial sequence
<220> FEATURE:
<223> OTHER INFORMATION: Description of artificial sequence: Synthetic Antisense
      Oligonucleotide

<400> SEQUENCE: 6
cccccaactg caggatgcct ttgtggaact gtacgg                          36

<210> SEQ ID NO 7
<211> LENGTH: 20
<212> TYPE: DNA
<213> ORGANISM: Artificial sequence
<220> FEATURE:
<223> OTHER INFORMATION: Description of artificial sequence: Synthetic Antisense
      Oligonucleotide

<400> SEQUENCE: 7
gggaaggatg gcgcacgctg                                            20

<210> SEQ ID NO 8
<211> LENGTH: 17
<212> TYPE: DNA
<213> ORGANISM: Artificial sequence
<220> FEATURE:
<223> OTHER INFORMATION: Description of artificial sequence: Synthetic Antisense
      Oligonucleotide

<400> SEQUENCE: 8
cgcgtgcgac cctcttg                                               17

<210> SEQ ID NO 9
<211> LENGTH: 17
<212> TYPE: DNA
<213> ORGANISM: Artificial sequence
<220> FEATURE:
<223> OTHER INFORMATION: Description of artificial sequence: Synthetic Antisense
      Oligonucleotide

<400> SEQUENCE: 9
taccgcgtgc gaccctc                                               17

<210> SEQ ID NO 10
<211> LENGTH: 17
<212> TYPE: DNA
<213> ORGANISM: Artificial sequence
<220> FEATURE:
<223> OTHER INFORMATION: Description of artificial sequence: Synthetic Antisense
      Oligonucleotide

<400> SEQUENCE: 10
```

```
        tcctaccgcg tgcgacc                                                17
```

<210> SEQ ID NO 11
<211> LENGTH: 17
<212> TYPE: DNA
<213> ORGANISM: Artificial sequence
<220> FEATURE:
<223> OTHER INFORMATION: Description of artificial sequence: Synthetic Antisense
      Oligonucleotide

<400> SEQUENCE: 11

```
        ccttcctacc gcgtgcg                                                17
```

<210> SEQ ID NO 12
<211> LENGTH: 17
<212> TYPE: DNA
<213> ORGANISM: Artificial sequence
<220> FEATURE:
<223> OTHER INFORMATION: Description of artificial sequence: Synthetic Antisense
      Oligonucleotide

<400> SEQUENCE: 12

```
        gacccttcct accgcgt                                                17
```

<210> SEQ ID NO 13
<211> LENGTH: 17
<212> TYPE: DNA
<213> ORGANISM: Artificial sequence
<220> FEATURE:
<223> OTHER INFORMATION: Description of artificial sequence: Synthetic Antisense
      Oligonucleotide

<400> SEQUENCE: 13

```
        ggagaccctt cctaccg                                                17
```

<210> SEQ ID NO 14
<211> LENGTH: 15
<212> TYPE: DNA
<213> ORGANISM: Artificial sequence
<220> FEATURE:
<223> OTHER INFORMATION: Description of artificial sequence: Synthetic Antisense
      Oligonucleotide

<400> SEQUENCE: 14

```
        gcggcggcag cgcgg                                                  15
```

<210> SEQ ID NO 15
<211> LENGTH: 15
<212> TYPE: DNA
<213> ORGANISM: Artificial sequence
<220> FEATURE:
<223> OTHER INFORMATION: Description of artificial sequence: Synthetic Antisense
      Oligonucleotide

<400> SEQUENCE: 15

```
        cggcggggcg acgga                                                  15
```

<210> SEQ ID NO 16
<211> LENGTH: 16
<212> TYPE: DNA
<213> ORGANISM: Artificial sequence
<220> FEATURE:
<223> OTHER INFORMATION: Description of artificial sequence: Synthetic Antisense
      Oligonucleotide

<400> SEQUENCE: 16

```
        cgggagcgcg gcgggc                                                 16
```

<210> SEQ ID NO 17
<211> LENGTH: 18
<212> TYPE: DNA
<213> ORGANISM: Artificial sequence
<220> FEATURE:
<223> OTHER INFORMATION: Description of artificial sequence: Synthetic Antisense Oligonucleotide

<400> SEQUENCE: 17
tctcccagcg tgcgccat                                             18

<210> SEQ ID NO 18
<211> LENGTH: 18
<212> TYPE: DNA
<213> ORGANISM: Artificial sequence
<220> FEATURE:
<223> OTHER INFORMATION: Description of artificial sequence: Synthetic Antisense Oligonucleotide

<400> SEQUENCE: 18
tgcactcacg ctcggcct                                             18

<210> SEQ ID NO 19
<211> LENGTH: 106
<212> TYPE: DNA
<213> ORGANISM: Artificial sequence
<220> FEATURE:
<223> OTHER INFORMATION: Description of artificial sequence: Synthetic Antisense Oligonucleotide

<400> SEQUENCE: 19
gcgcccgccc ctccgcgccg cctgcccgcc cgcccgccgc gctcccgccc gccgctctcc   60
ccttattgtt aaaaacatgt tagaagcaat gaatgtatat aaaagc                106

<210> SEQ ID NO 20
<211> LENGTH: 717
<212> TYPE: DNA
<213> ORGANISM: Homo Sapiens
<220> FEATURE:
<221> NAME/KEY: CDS
<222> LOCATION: (1)...(717)

<400> SEQUENCE: 20

```
atg gcg cac gct ggg aga acg ggg tac gac aac cgg gag ata gtg atg    48
Met Ala His Ala Gly Arg Thr Gly Tyr Asp Asn Arg Glu Ile Val Met
  1               5                  10                  15
aag tac atc cat tat aag ctg tcg cag agg ggc tac gag tgg gat gcg    96
Lys Tyr Ile His Tyr Lys Leu Ser Gln Arg Gly Tyr Glu Trp Asp Ala
             20                  25                  30
gga gat gtg ggc gcc gcg ccc ccg ggg gcc gcc ccc gca ccg ggc atc   144
Gly Asp Val Gly Ala Ala Pro Pro Gly Ala Ala Pro Ala Pro Gly Ile
         35                  40                  45
ttc tcc tcc cag ccc ggg cac acg ccc cat cca gcc gca tcc cgc gac   192
Phe Ser Ser Gln Pro Gly His Thr Pro His Pro Ala Ala Ser Arg Asp
     50                  55                  60
ccg gtc gcc agg acc tcg ccg ctg cag acc ccg gct gcc ccc ggc gcc   240
Pro Val Ala Arg Thr Ser Pro Leu Gln Thr Pro Ala Ala Pro Gly Ala
 65                  70                  75                  80
gcc gcg ggg cct gcg ctc agc ccg gtg cca cct gtg gtc cac ctg gcc   288
Ala Ala Gly Pro Ala Leu Ser Pro Val Pro Pro Val Val His Leu Ala
                 85                  90                  95
ctc cgc caa gcc ggc gac gac ttc tcc cgc cgc tac cgc ggc gac ttc   336
Leu Arg Gln Ala Gly Asp Asp Phe Ser Arg Arg Tyr Arg Gly Asp Phe
            100                 105                 110
gcc gag atg tcc agc cag ctg cac ctg acg ccc ttc acc gcg cgg gga   384
Ala Glu Met Ser Ser Gln Leu His Leu Thr Pro Phe Thr Ala Arg Gly
        115                 120                 125
cgc ttt gcc acg gtg gtg gag gag ctc ttc agg gac ggg gtg aac tgg   432
Arg Phe Ala Thr Val Val Glu Glu Leu Phe Arg Asp Gly Val Asn Trp
    130                 135                 140
```

```
ggg agg att gtg gcc ttc ttt gag ttc ggt ggg gtc atg tgt gtg gag       480
Gly Arg Ile Val Ala Phe Phe Glu Phe Gly Gly Val Met Cys Val Glu
145                 150                 155                 160
agc gtc aac cgg gag atg tcg ccc ctg gtg gac aac atc gcc ctg tgg       528
Ser Val Asn Arg Glu Met Ser Pro Leu Val Asp Asn Ile Ala Leu Trp
                165                 170                 175
atg act gag tac ctg aac cgg cac ctg cac acc tgg atc cag gat aac       576
Met Thr Glu Tyr Leu Asn Arg His Leu His Thr Trp Ile Gln Asp Asn
            180                 185                 190
gga ggc tgg gat gcc ttt gtg gaa ctg tac ggc ccc agc atg cgg cct       624
Gly Gly Trp Asp Ala Phe Val Glu Leu Tyr Gly Pro Ser Met Arg Pro
        195                 200                 205
ctg ttt gat ttc tcc tgg ctg tct ctg aag act ctg ctc agt ttg gcc       672
Leu Phe Asp Phe Ser Trp Leu Ser Leu Lys Thr Leu Leu Ser Leu Ala
    210                 215                 220
ctg gtg gga gct tgc atc acc ctg ggt gcc tat ctg agc cac aag           717
Leu Val Gly Ala Cys Ile Thr Leu Gly Ala Tyr Leu Ser His Lys
225                 230                 235
```

<210> SEQ ID NO 21
<211> LENGTH: 239
<212> TYPE: PRT
<213> ORGANISM: Homo Sapiens

<400> SEQUENCE: 21

```
Met Ala His Ala Gly Arg Thr Gly Tyr Asp Asn Arg Glu Ile Val Met
1               5                   10                  15
Lys Tyr Ile His Tyr Lys Leu Ser Gln Arg Gly Tyr Glu Trp Asp Ala
            20                  25                  30
Gly Asp Val Gly Ala Ala Pro Pro Gly Ala Ala Pro Ala Pro Gly Ile
        35                  40                  45
Phe Ser Ser Gln Pro Gly His Thr Pro His Pro Ala Ala Ser Arg Asp
    50                  55                  60
Pro Val Ala Arg Thr Ser Pro Leu Gln Thr Pro Ala Ala Pro Gly Ala
65                  70                  75                  80
Ala Ala Gly Pro Ala Leu Ser Pro Val Pro Pro Val Val His Leu Ala
                85                  90                  95
Leu Arg Gln Ala Gly Asp Asp Phe Ser Arg Arg Tyr Arg Gly Asp Phe
            100                 105                 110
Ala Glu Met Ser Ser Gln Leu His Leu Thr Pro Phe Thr Ala Arg Gly
        115                 120                 125
Arg Phe Ala Thr Val Val Glu Glu Leu Phe Arg Asp Gly Val Asn Trp
    130                 135                 140
Gly Arg Ile Val Ala Phe Phe Glu Phe Gly Gly Val Met Cys Val Glu
145                 150                 155                 160
Ser Val Asn Arg Glu Met Ser Pro Leu Val Asp Asn Ile Ala Leu Trp
                165                 170                 175
Met Thr Glu Tyr Leu Asn Arg His Leu His Thr Trp Ile Gln Asp Asn
            180                 185                 190
Gly Gly Trp Asp Ala Phe Val Glu Leu Tyr Gly Pro Ser Met Arg Pro
        195                 200                 205
Leu Phe Asp Phe Ser Trp Leu Ser Leu Lys Thr Leu Leu Ser Leu Ala
    210                 215                 220
Leu Val Gly Ala Cys Ile Thr Leu Gly Ala Tyr Leu Ser His Lys
225                 230                 235
```

<210> SEQ ID NO 22
<211> LENGTH: 615
<212> TYPE: DNA
<213> ORGANISM: Homo Sapiens
<220> FEATURE:
<221> NAME/KEY: CDS
<222> LOCATION: (1)...(615)

<400> SEQUENCE: 22

```
atg gcg cac gct ggg aga acg ggg tac gac aac cgg gag ata gtg atg        48
Met Ala His Ala Gly Arg Thr Gly Tyr Asp Asn Arg Glu Ile Val Met
1               5                   10                  15
aag tac atc cat tat aag ctg tcg cag agg ggc tac gag tgg gat gcg        96
Lys Tyr Ile His Tyr Lys Leu Ser Gln Arg Gly Tyr Glu Trp Asp Ala
            20                  25                  30
gga gat gtg ggc gcc gcg ccc ccg ggg gcc gcc ccc gca ccg ggc atc       144
Gly Asp Val Gly Ala Ala Pro Pro Gly Ala Ala Pro Ala Pro Gly Ile
        35                  40                  45
ttc tcc tcc cag ccc ggg cac acg ccc cat cca gcc gca tcc cgc gac       192
```

```
    Phe Ser Ser Gln Pro Gly His Thr Pro His Pro Ala Ala Ser Arg Asp
         50                  55                  60
ccg gtc gcc agg acc tcg ccg ctg cag acc ccg gct gcc ccc ggc gcc       240
Pro Val Ala Arg Thr Ser Pro Leu Gln Thr Pro Ala Ala Pro Gly Ala
 65                  70                  75                  80
gcc gcg ggg cct gcg ctc agc ccg gtg cca cct gtg gtc cac ctg gcc       288
Ala Ala Gly Pro Ala Leu Ser Pro Val Pro Pro Val Val His Leu Ala
                 85                  90                  95
ctc cgc caa gcc ggc gac gac ttc tcc cgc cgc tac cgc ggc gac ttc       336
Leu Arg Gln Ala Gly Asp Asp Phe Ser Arg Arg Tyr Arg Gly Asp Phe
            100                 105                 110
gcc gag atg tcc agc cag ctg cac ctg acg ccc ttc acc gcg cgg gga       384
Ala Glu Met Ser Ser Gln Leu His Leu Thr Pro Phe Thr Ala Arg Gly
        115                 120                 125
cgc ttt gcc acg gtg gtg gag gag ctc ttc agg gac ggg gtg aac tgg       432
Arg Phe Ala Thr Val Val Glu Glu Leu Phe Arg Asp Gly Val Asn Trp
    130                 135                 140
ggg agg att gtg gcc ttc ttt gag ttc ggt ggg gtc atg tgt gtg gag       480
Gly Arg Ile Val Ala Phe Phe Glu Phe Gly Gly Val Met Cys Val Glu
145                 150                 155                 160
agc gtc aac cgg gag atg tcg ccc ctg gtg gac aac atc gcc ctg tgg       528
Ser Val Asn Arg Glu Met Ser Pro Leu Val Asp Asn Ile Ala Leu Trp
                165                 170                 175
atg act gag tac ctg aac cgg cac ctg cac acc tgg atc cag gat aac       576
Met Thr Glu Tyr Leu Asn Arg His Leu His Thr Trp Ile Gln Asp Asn
            180                 185                 190
gga ggc tgg gta ggt gca tct ggt gat gtg agt ctg ggc                   615
Gly Gly Trp Val Gly Ala Ser Gly Asp Val Ser Leu Gly
        195                 200                 205
```

<210> SEQ ID NO 23
<211> LENGTH: 205
<212> TYPE: PRT
<213> ORGANISM: Homo Sapiens

<400> SEQUENCE: 23

```
Met Ala His Ala Gly Arg Thr Gly Tyr Asp Asn Arg Glu Ile Val Met
  1               5                  10                  15
Lys Tyr Ile His Tyr Lys Leu Ser Gln Arg Gly Tyr Glu Trp Asp Ala
                 20                  25                  30
Gly Asp Val Gly Ala Ala Pro Pro Gly Ala Ala Pro Ala Pro Gly Ile
             35                  40                  45
Phe Ser Ser Gln Pro Gly His Thr Pro His Pro Ala Ala Ser Arg Asp
         50                  55                  60
Pro Val Ala Arg Thr Ser Pro Leu Gln Thr Pro Ala Ala Pro Gly Ala
 65                  70                  75                  80
Ala Ala Gly Pro Ala Leu Ser Pro Val Pro Pro Val Val His Leu Ala
                 85                  90                  95
Leu Arg Gln Ala Gly Asp Asp Phe Ser Arg Arg Tyr Arg Gly Asp Phe
            100                 105                 110
Ala Glu Met Ser Ser Gln Leu His Leu Thr Pro Phe Thr Ala Arg Gly
        115                 120                 125
Arg Phe Ala Thr Val Val Glu Glu Leu Phe Arg Asp Gly Val Asn Trp
    130                 135                 140
Gly Arg Ile Val Ala Phe Phe Glu Phe Gly Gly Val Met Cys Val Glu
145                 150                 155                 160
Ser Val Asn Arg Glu Met Ser Pro Leu Val Asp Asn Ile Ala Leu Trp
                165                 170                 175
Met Thr Glu Tyr Leu Asn Arg His Leu His Thr Trp Ile Gln Asp Asn
            180                 185                 190
Gly Gly Trp Val Gly Ala Ser Gly Asp Val Ser Leu Gly
        195                 200                 205
```

<210> SEQ ID NO 24
<211> LENGTH: 18
<212> TYPE: DNA
<213> ORGANISM: Artificial sequence
<220> FEATURE:
<223> OTHER INFORMATION: Description of artificial sequence: Synthetic Antisense
      Oligonucleotide

<400> SEQUENCE: 24
tctcccagcg tgcgccat                                                18

-continued

<210> SEQ ID NO 25
<211> LENGTH: 18
<212> TYPE: DNA
<213> ORGANISM: Artificial sequence
<220> FEATURE:
<223> OTHER INFORMATION: Description of artificial sequence: Synthetic Antisense
      Oligonucleotide

<400> SEQUENCE: 25
tgcactcacg ctcggcct                                              18

<210> SEQ ID NO 26
<211> LENGTH: 20
<212> TYPE: DNA
<213> ORGANISM: Artificial sequence
<220> FEATURE:
<223> OTHER INFORMATION: Description of artificial sequence: Synthetic Antisense
      Oligonucleotide

<400> SEQUENCE: 26
gcgcggcggg cgggcgggca                                            20

<210> SEQ ID NO 27
<211> LENGTH: 20
<212> TYPE: DNA
<213> ORGANISM: Artificial sequence
<220> FEATURE:
<223> OTHER INFORMATION: Description of artificial sequence: Synthetic Antisense
      Oligonucleotide

<400> SEQUENCE: 27
gggcggaggc cggccggcgg                                            20

<210> SEQ ID NO 28
<211> LENGTH: 20
<212> TYPE: DNA
<213> ORGANISM: Artificial sequence
<220> FEATURE:
<223> OTHER INFORMATION: Description of artificial sequence: Synthetic Antisense
      Oligonucleotide

<400> SEQUENCE: 28
agcggcggcg gcggcagcgc                                            20

<210> SEQ ID NO 29
<211> LENGTH: 20
<212> TYPE: DNA
<213> ORGANISM: Artificial sequence
<220> FEATURE:
<223> OTHER INFORMATION: Description of artificial sequence: Synthetic Antisense
      Oligonucleotide

<400> SEQUENCE: 29
gggccgggaa gggcgcccgc                                            20

<210> SEQ ID NO 30
<211> LENGTH: 84
<212> TYPE: DNA
<213> ORGANISM: Artificial Sequence
<220> FEATURE:
<223> OTHER INFORMATION: Description of artificial sequence: Synthetic Antisense
      Oligonucleotide

<400> SEQUENCE: 30
ttcagcaaaa atgtcgacat atcttccaca cccccctggt tctgacctct cagcaaggca    60
    tttggctttg aaaggccgtt ttgt                                           84

```
<210> SEQ ID NO 31
<211> LENGTH: 67
<212> TYPE: DNA
<213> ORGANISM: Artificial Sequence
<220> FEATURE:
<223> OTHER INFORMATION: Description of artificial sequence: Synthetic Antisense
      Oligonucleotide

<400> SEQUENCE: 31
gaccgcattt tcaaaaagct gctctgagag tagatgacgt aaataaagcc cttgtaacag    60
    tgacgta                                                              67

<210> SEQ ID NO 32
<211> LENGTH: 29
<212> TYPE: DNA
<213> ORGANISM: Artificial Sequence
<220> FEATURE:
<223> OTHER INFORMATION: Description of artificial sequence: Synthetic Antisense
      Oligonucleotide

<400> SEQUENCE: 32
cccttcaccc acctagctct gtcccgcag                                      29

<210> SEQ ID NO 33
<211> LENGTH: 34
<212> TYPE: DNA
<213> ORGANISM: Artificial Sequence
<220> FEATURE:
<223> OTHER INFORMATION: Description of artificial sequence: Synthetic Antisense
      Oligonucleotide

<400> SEQUENCE: 33
tgacgtcatc tcccagcgtg cgccattgac gtca                                34

<210> SEQ ID NO 34
<211> LENGTH: 52
<212> TYPE: DNA
<213> ORGANISM: Artificial Sequence
<220> FEATURE:
<223> OTHER INFORMATION: Description of artificial sequence: Synthetic Antisense
      Oligonucleotide

<400> SEQUENCE: 34
tgacgtcatc tcccagcgtg cgccattctc ccagcgtgcg ccattgacgt ca            52

<210> SEQ ID NO 35
<211> LENGTH: 34
<212> TYPE: DNA
<213> ORGANISM: Artificial Sequence
<220> FEATURE:
<223> OTHER INFORMATION: Description of artificial sequence: Synthetic Antisense
      Oligonucleotide

<400> SEQUENCE: 35
tgacgtcatc tcccagcgtg cgccattgac gtca                                34

<210> SEQ ID NO 36
<211> LENGTH: 24
<212> TYPE: DNA
<213> ORGANISM: Artificial Sequence
<220> FEATURE:
<223> OTHER INFORMATION: Description of artificial sequence: Synthetic Antisense
      Oligonucleotide

<400> SEQUENCE: 36
tgacgtcatg acgtcatgac gtca                                           24
```

```
<210> SEQ ID NO 37
<211> LENGTH: 20
<212> TYPE: DNA
<213> ORGANISM: Artificial Sequence
<220> FEATURE:
<223> OTHER INFORMATION: Description of artificial sequence: Synthetic Antisense
      Oligonucleotide

<400> SEQUENCE: 37
tgacgtcatt tttgacgtca                                                   20

<210> SEQ ID NO 38
<211> LENGTH: 19
<212> TYPE: DNA
<213> ORGANISM: Artificial Sequence
<220> FEATURE:
<223> OTHER INFORMATION: Description of artificial sequence: Synthetic Antisense
      Oligonucleotide

<400> SEQUENCE: 38
tgacgtcatt ttgacgtca                                                    19

<210> SEQ ID NO 39
<211> LENGTH: 18
<212> TYPE: DNA
<213> ORGANISM: Artificial Sequence
<220> FEATURE:
<223> OTHER INFORMATION: Description of artificial sequence: Synthetic Antisense
      Oligonucleotide

<400> SEQUENCE: 39
tgacgtcatt tgacgtca                                                     18

<210> SEQ ID NO 40
<211> LENGTH: 17
<212> TYPE: DNA
<213> ORGANISM: Artificial Sequence
<220> FEATURE:
<223> OTHER INFORMATION: Description of artificial sequence: Synthetic Antisense
      Oligonucleotide

<400> SEQUENCE: 40
tgacgtcatt gacgtca                                                      17

<210> SEQ ID NO 41
<211> LENGTH: 34
<212> TYPE: DNA
<213> ORGANISM: Artificial Sequence
<220> FEATURE:
<223> OTHER INFORMATION: Description of artificial sequence: Synthetic Antisense
      Oligonucleotide

<400> SEQUENCE: 41
tgacgtcatc tcccagcgtg cgccattgac gtca                                   34

<210> SEQ ID NO 42
<211> LENGTH: 23
<212> TYPE: DNA
<213> ORGANISM: Artificial Sequence
<220> FEATURE:
<223> OTHER INFORMATION: Description of artificial sequence: Synthetic Antisense
      Oligonucleotide

<400> SEQUENCE: 42
aggatggcgc acgctgggag aac                                               23

<210> SEQ ID NO 43
```

```
-continued

<211> LENGTH: 57
<212> TYPE: DNA
<213> ORGANISM: Artificial Sequence
<220> FEATURE:
<223> OTHER INFORMATION: Description of artificial sequence: Synthetic Antisense
      Oligonucleotide

<400> SEQUENCE: 43
tgacgtcatc tcccagcgtg cgccattgac gtcaacagag ggtcgcacgc ggtagga    57
```